United States Patent
Patel et al.

(10) Patent No.: US 9,282,972 B1
(45) Date of Patent: Mar. 15, 2016

(54) SURGICAL CLIPS WITH PENETRATING LOCKING MECHANISM AND NON-SLIP CLAMPING SURFACES

(71) Applicants: Manoj B. Patel, Lumberton, NJ (US); Bhailal H. Patel, Kendall Park, NJ (US); David M. Albala, Manlius, NY (US)

(72) Inventors: Manoj B. Patel, Lumberton, NJ (US); Bhailal H. Patel, Kendall Park, NJ (US); David M. Albala, Manlius, NY (US)

(73) Assignee: INNOVATIVE UROLOLY, LLC, Austin, TX (US)

(*) Notice: Subject to any disclaimer, the term of this patent is extended or adjusted under 35 U.S.C. 154(b) by 95 days.

(21) Appl. No.: 14/053,695

(22) Filed: Oct. 15, 2013

Related U.S. Application Data

(60) Provisional application No. 61/713,599, filed on Oct. 14, 2012.

(51) Int. Cl.
*A61B 17/08* (2006.01)
*A61B 17/122* (2006.01)

(52) U.S. Cl.
CPC ............. *A61B 17/122* (2013.01); *A61B 17/083* (2013.01); *A61B 17/1227* (2013.01)

(58) Field of Classification Search
CPC .. A61B 17/122; A61B 17/1227; A61B 17/08; A61B 17/083; A61B 17/1285; A61B 17/12; A61B 17/0487; A61B 2017/1107; A61B 2017/1225; A61B 2017/12004; A61B 2017/00584; A61B 5/6884; A61F 6/206; A61F 6/20; Y10T 24/44538; Y10T 24/44752; Y10T 24/44274

USPC ......... 606/157, 158, 151; 24/132 WL, 132 R, 24/489, 517–519, 521; 206/159, 340
See application file for complete search history.

(56) References Cited

U.S. PATENT DOCUMENTS

| | | | | | |
|---|---|---|---|---|---|
| 4,579,118 | A | * | 4/1986 | Failla | 606/158 |
| 4,976,722 | A | * | 12/1990 | Failla | 606/157 |
| 5,330,442 | A | * | 7/1994 | Green | A61B 17/0487 606/151 |
| 5,921,991 | A | * | 7/1999 | Whitehead et al. | 606/120 |
| 6,421,920 | B1 | * | 7/2002 | Jensen | 30/134 |
| 2005/0165423 | A1 | * | 7/2005 | Gallagher | A61B 17/122 606/151 |
| 2006/0217749 | A1 | * | 9/2006 | Wilson, Jr. | A61B 17/122 606/157 |
| 2009/0171380 | A1 | * | 7/2009 | Whiting | 606/158 |

FOREIGN PATENT DOCUMENTS

EP 122046 A * 10/1984

* cited by examiner

*Primary Examiner* — Katrina Stransky
*Assistant Examiner* — Katherine Schwiker
(74) *Attorney, Agent, or Firm* — Rick B. Yeager

(57) ABSTRACT

A surgical clip includes a pair of opposed arms joined at one end by an integrally formed flexible hinge and a hinge lock. A male locking pin near the free end of one arm is configured to penetrate tissue when the male locking pin is urged towards a mating female aperture near the end of the opposite arm. The clamping side of an arm may include a protruding feature, such as a wedge shape elongated ridge, while the clamping side of the opposite arm includes a corresponding trough or aperture that receives the protruding feature. Clamping surfaces may include non-slip protrusions, such as ribs, ridges, cones or pins. An applicator holding feature, such as a boss, near the hinge prevents the clip from yawing and becoming askew during application.

11 Claims, 31 Drawing Sheets

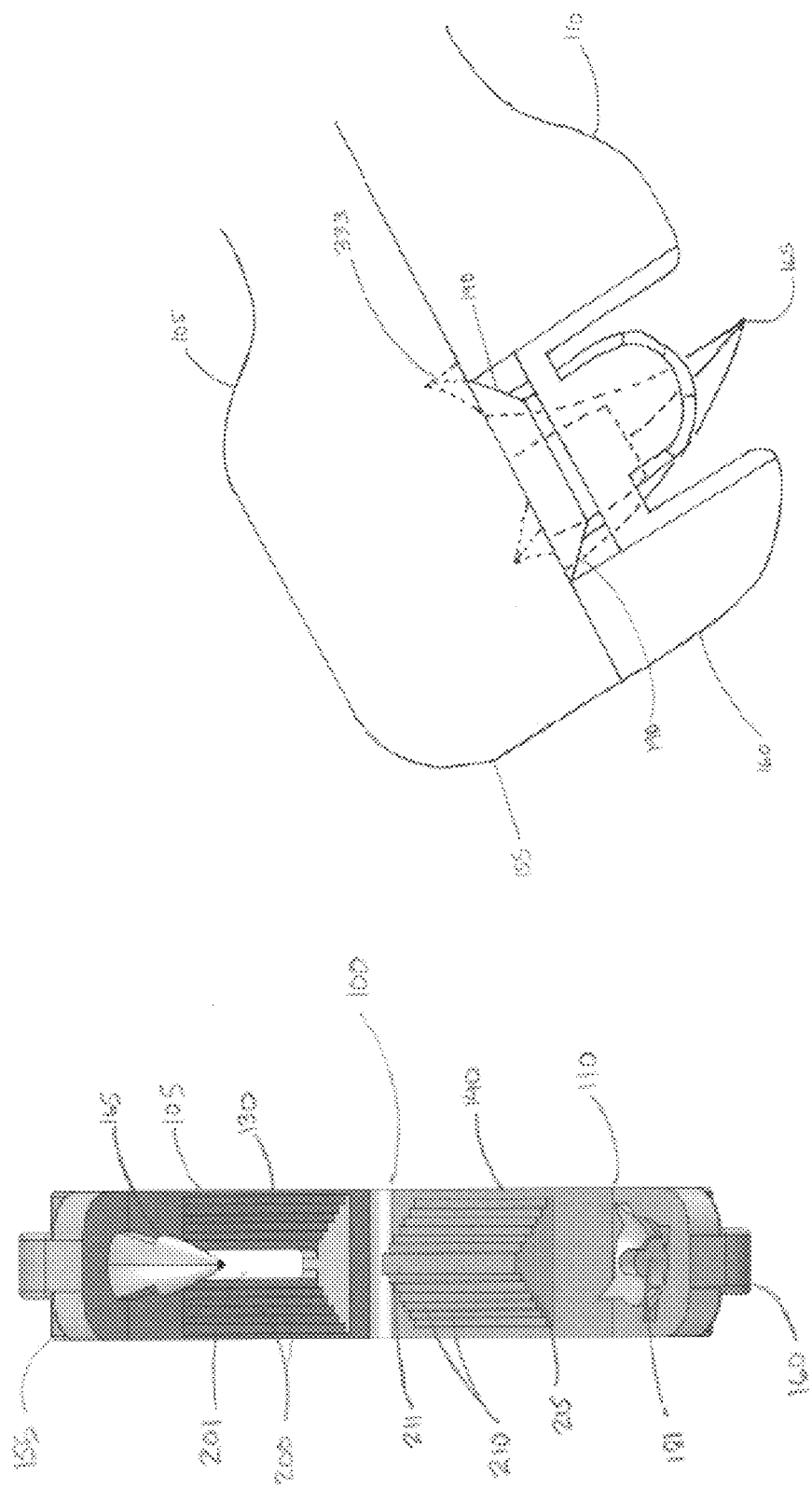

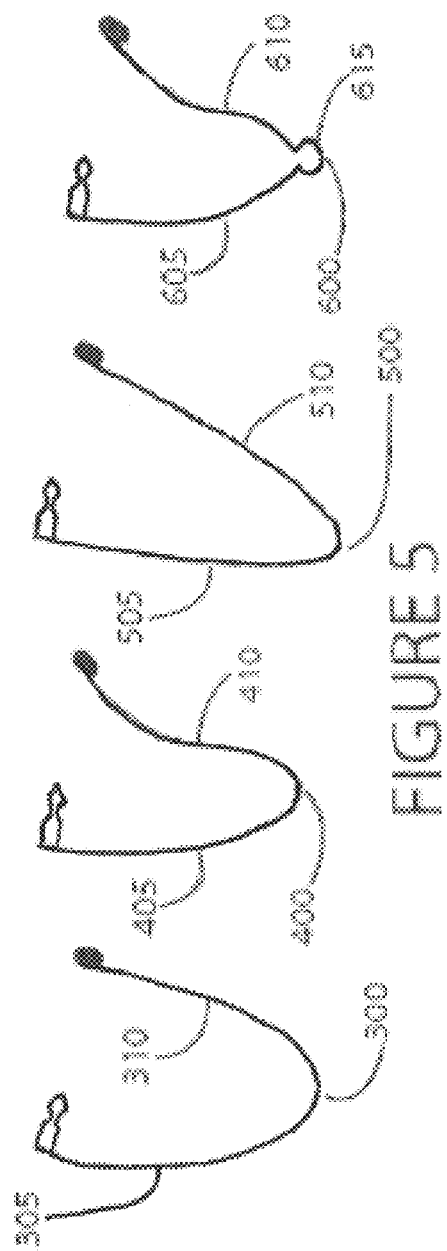

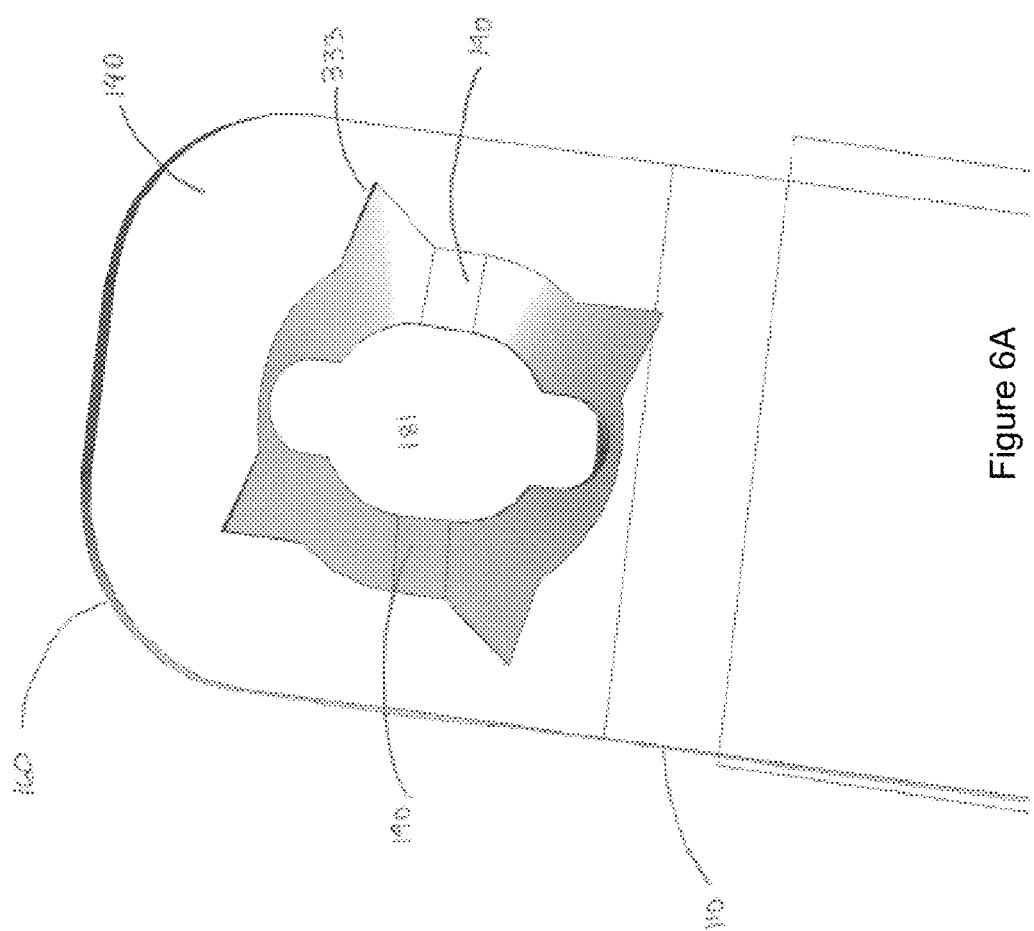

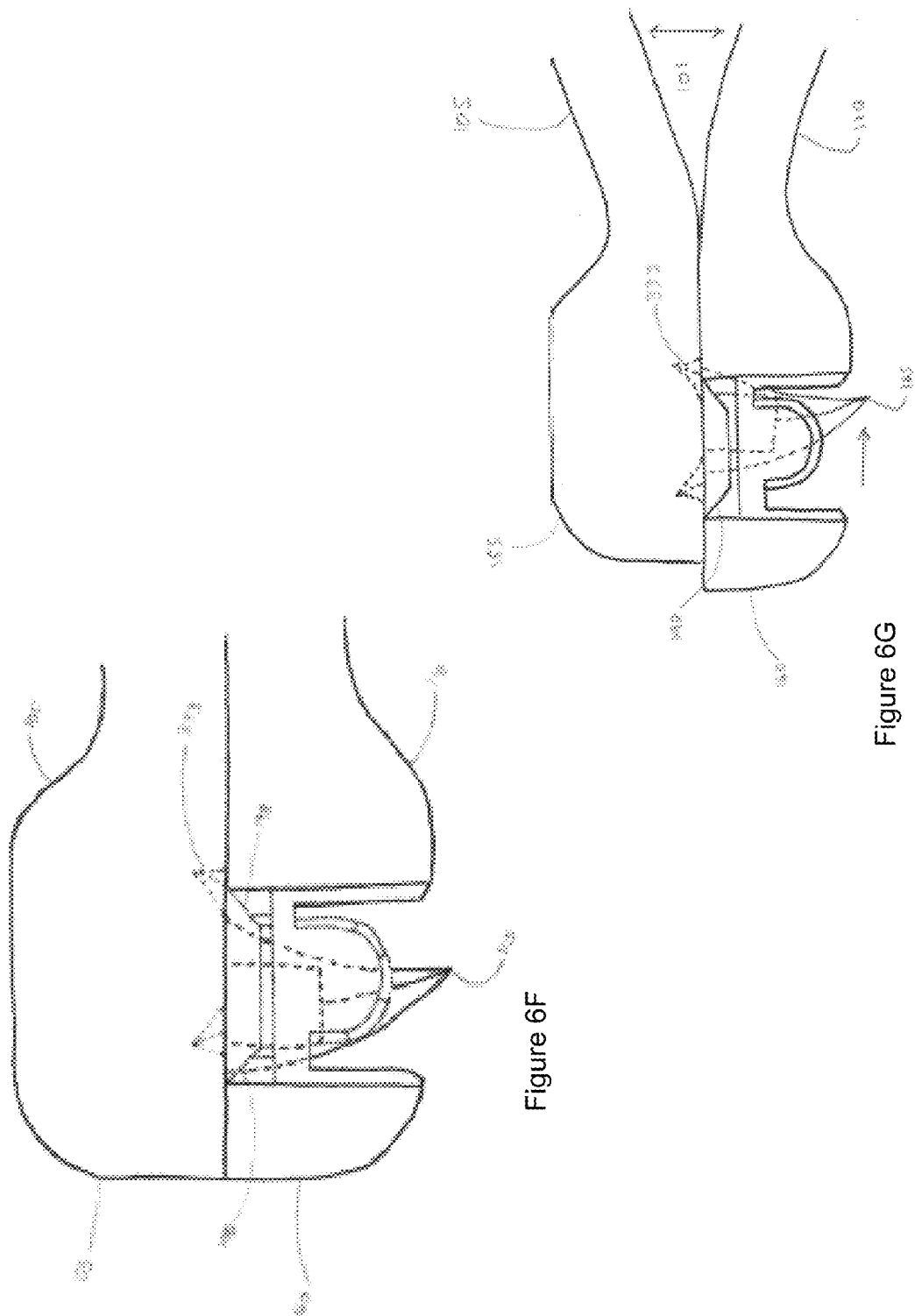

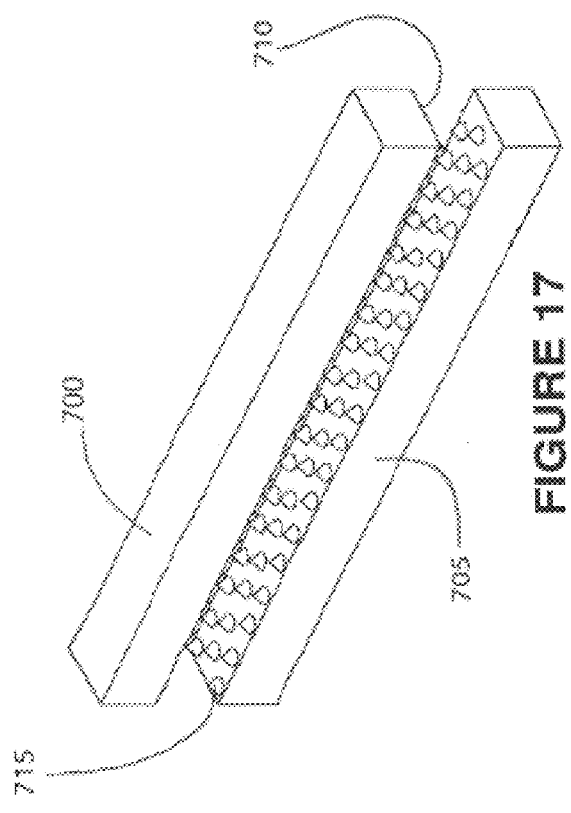
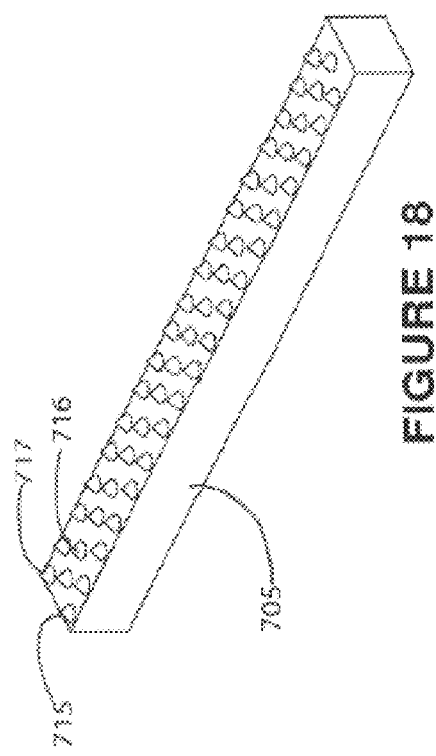

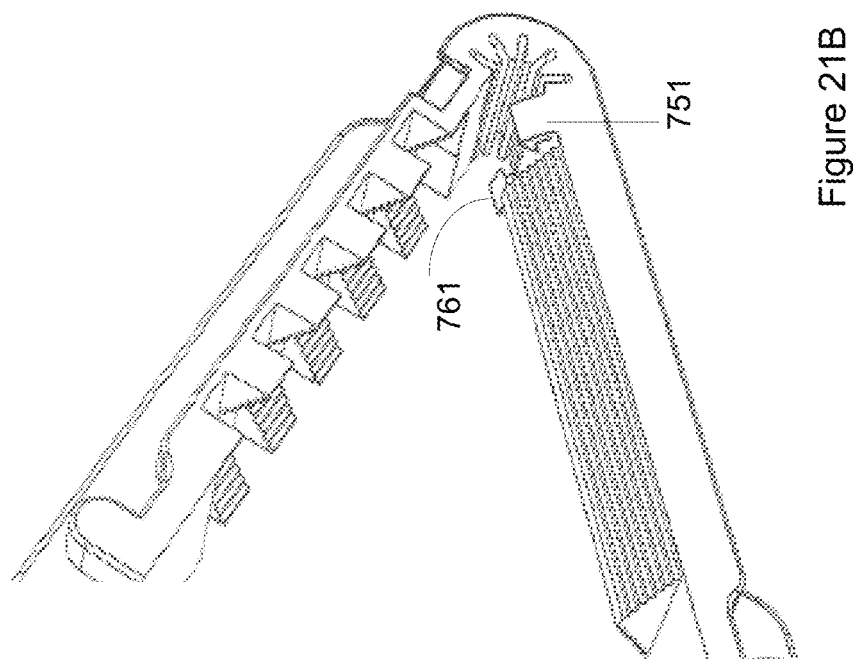

SURGICAL CLIPS WITH PENETRATING LOCKING MECHANISM AND NON-SLIP CLAMPING SURFACES

RELATED APPLICATIONS

This non-provisional U.S. patent application is related to U.S. Provisional Application No. 61/713,599 filed on Oct. 14, 2012, and claims the benefit of that filing date.

FIELD OF THE INVENTION

The present invention relates to surgical clips, and, more particularly, to a biocompatible surgical clip with grooved clamping surfaces to prevent slipping, a tissue penetrating head lock mechanism, and a locking hinge portion to provide greater tension and security when clamping tissue between the two arms of the clip.

BACKGROUND

A wide number of surgical procedures employ surgical clips (i.e., ligation clips). Such surgical procedures may require vessels, organs or other tissues of the human body to be ligated. Surgical clips ligate, clamp, close off or otherwise occlude the engaged portion of the clamped vessels, organs or other tissues in a surgical site. Such clips may also be used to secure the ends of a suture, as in place of a conventional suture knot.

Ligation can be performed with a ligating clip (i.e., a surgical clip) or by suturing with surgical thread. Suturing requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. So long as the clips and applicator are designed with endoscopic procedures in mind, they are a preferred choice.

The clips are often in the form of thin, narrow, metal or polymeric U-shaped or V-shaped members that are placed over the vessel, tissue or suture material and then forced into a closed position using a clip applicator. Clips constructed of metal, may be initially open and then permanently deformed into a closed or clamped configuration around the desired blood vessel or other tissue structure using an appropriate clip applicator. However, metal clips, which are radio-opaque, interfere with x-ray imaging. Plastic clips include a latch feature to ensure that the clip remains closed with sufficient force to provide full and complete hemostasis or occlusion and to ensure that the clip will not loosen or open over time.

While ligating clips are an improvement over suturing in many procedures, they suffer shortcomings. First the clips typically require a surgical plane or window to be made prior to attachment. Conventional clips are not configured to penetrate tissue. Accurate planing and windowing manipulations are time-consuming and difficult to perform, particularly in endoscopic surgical procedures, which are characterized by limited space and visibility. Furthermore, creating windows can cause extensive bleeding, leading to decreased visibility.

Second, the clips tend to slip as they are applied. Slipping makes accurate placement extremely difficult. Additionally, forces applied during slipping may cause the contact surfaces of the clamping arms to deviate from parallel. In a worst case scenario, slipping may result in catastrophic dislodgment of the clip, resulting in excessive bleeding and increased mortality and morbidity.

Third, the clips are extremely difficult to remove. Conventional clips include relatively thick hinge and arm sections that abut and occlude a clamped vessel or tissue. The latch is not releasable. Cutting through such a clip without damaging the clamped vessel or tissue is extremely difficult.

U.S. Patent Publication No. 2012/0083803 is incorporated by reference in this specification. That patent application describes a penetrating lock and various clamping features, hinge configurations, and boss configurations.

The invention is directed to overcoming one or more of the problems and solving one or more of the needs as set forth above.

SUMMARY OF THE INVENTION

To solve one or more of the problems set forth above, in an exemplary implementation of the invention, a surgical clip includes a pair of opposed arms joined at one end by an integrally formed flexible hinge. Each arm has a free end. One arm includes a male locking pin near the free end. The opposite arm includes a female aperture near the free end. The male locking pin is configured to penetrate tissue in the path of the male locking pin when the male locking pin is urged towards the female aperture. The male locking pin includes a tissue penetrating head which may be a tissue spreading head. The female aperture engages the male locking pin and resists withdrawal of the head when the head of the male locking pin has been urged through the female aperture. The clip may be comprised of a biocompatible metal or plastic or a bioabsorbable plastic. The clip may be comprised of hybrid material with various components of metal and polymer or carbon fiber material. Each of the pair of arms includes a clamping side.

In one embodiment, the clamping side of one arm includes a wedge-shaped feature. The clamping side of the second arm includes a V-shaped trough that conforms to the shape of the wedge shaped feature. Each clamping side includes non-slip protrusions such as non-slip protruding ribs, cones, teeth, or needles. The integrally formed flexible hinge has a reduced thickness and protrudes outwardly from the clamping surfaces of the arms. The hinge may be cut to release the clip without cutting the clamped tissue or vessel.

In an exemplary surgical clip, a pair of opposed arms are joined at a hinged proximal end by an integrally formed flexible hinge. Each arm has a free distal end. One arm includes a male locking pin near the free distal end. The opposite arm includes a female aperture near the free end. The male locking pin includes a tissue piercing head configured to penetrate tissue in the path of the male locking pin when the male locking pin is urged towards the female aperture. The male pin acts as a penetrating trocar via spreading the tissue fibers so it pierces the tissue in an atraumatic fashion. As the male pin punctures the tissue, it perforates and tunnels (or bores) through the tissue to create a tissue channel/opening atraumatically. The female aperture includes a shape that engages the male locking pin and resists withdrawal of the head when the head of the male locking pin has been urged through the female aperture.

In one embodiment as depicted in FIG. 6D-6E, the female aperture is oval-shaped to allow the male pin to sit securely when clamping various thicknesses of tissue. When thick tissue is clamped between the arms of the clip, the two arms will bow outward, causing the male and female ends to fit insecurely under intense strain—predisposing it to not close securely or "pop-open" once it is clamped closed. Since the female aperture is oval-shaped, the male pin can fit into the female receptacle securely when clamping thick tissue; the oblong/oval female aperture accommodates the male pin to slide within the receptacle to allow the bowing of the clip arms without strain or tension on the male-female engagement.

In an exemplary surgical clip, the flexible hinge is a U-shaped segment that extends from the hinged end of each arm of the pair of opposed arms. The hinged ends of the arms are configured to abut each other when the surgical clip is closed. A curved hinge guard prevents tissue from invading the flexible hinge, while ensuring that the clamping arms maintain intimate contact with the clamped tissue. A clamped object (e.g., tissue) does not contact the flexible hinge when the surgical clip is closed and the hinge may be cut to release the clamp, without contacting the clamped object. An empty space is maintained between the hinged ends of the arms of the pair of opposed arms and the flexible hinge. The flexible hinge has a hinge thickness and width, and each arm of the pair of opposed arms has an average thickness and width. In one embodiment, the width and/or thickness of the flexible hinge is less than the average width of each arm of the pair of opposed arms to facilitate cutting. In one embodiment, the clip includes a locking hinge portion that locks the clip in the closed position when the male head element is engaged into the head mating element.

Therefore, when the clip is closed/engaged around tissue (blood vessels, etc.), there are two irreversible locking features that allow the clip to maintain tension on the tissue—one at the distal end of the clip where the male pin engages the female receptacle, and a hinge lock near the proximal end of the clip. The hinge lock provides improved clamping force, and accommodates a wide range of tissue thickness within the clamped arms without comprising the integrity of the hinge strength.

In one embodiment, to facilitate the male head element piercing the tissue via a spreading fashion, tissue anchor features are provided in proximity to the head mating element. In one example, the female receptacle is surrounded by several sharp pyramids that act like anchors to keep the tissue in-place, under tension, and in the stretched position while the male pin enters tissue—this mechanism allows the male pin to spread tissue apart laterally via shearing forces in opposite direction. This tissue spreading is depicted in FIGS. 20A-20E.

Optionally, the surgical clip may be comprised of a bioabsorbable plastic. Other materials include biocompatible metals, plastics and composites. Examples of suitable plastics include acetal polyoxymethylene (POM), polyethylene terephthalate (PET), polybutylene terephthalate (PBT), polyoxymethylene, polyetheretherketone (PEEK), polypropylene, and polyethylene or other thermoplastic materials having similar properties that can be injection-molded. The clip may be comprised of polymer material in combination with radiolucent metal alloys.

Each of the pair of arms includes a clamping side. In one embodiment, the clamping side of one arm includes a wedge-shaped feature. The clamping side of the second arm includes a V-shaped trough that conforms to the shape of the wedge shaped feature. Each clamping side includes non-slip protrusions, such as non-slip protruding ribs.

An alternative clip design includes one arm (either a female arm or a male arm) having a pair of elongated arms or spars separated by a space or gap. The gap between the spars receives an elongated wedge-shaped ridge projecting from the clamping surface of the opposite arm, when the arms are in a clamping position. The gap is wide enough to allow at least a portion of the ridge and clamped tissue or vessel to fit within the gap, thus preventing dislodgment of the clip during extreme pressure circumstances. In another embodiment, one arm includes a central window.

An exemplary clip includes a plurality of bosses, including a hinge boss, for gripping by an applicator and stabilizing during use. As used herein, a boss is a projection or protuberance that can be engaged by an applicator. The hinge boss is a grippable boss (i.e., a protrusion suitable for gripping) at or near the hinge. Gripping the hinge boss during use prevents undesirable angulation (angular disorientation) of the clip during use with an applicator. An alternative design to prevent undesired angulation of the clip during use with the applicator is to have rectangular-shaped bosses near the free end of each arm. Rectangular-shaped bosses maintain the alignment of the clip within the arms of the applicator while it is applied onto tissue, preventing the proximal end of the clip (the hinge region) from angulating out of the jaws of the applicator.

In one embodiment, the clip has a width of about 3.2 mm or more, as compared to about 1.6 mm for prior art polymer ligation clips. This extra width provides several advantages—it provides a greater clamping surface area between the clamp arms; it permits a relatively large, wide, and strong male pin feature to penetrate tissue; and it permits a relatively large diameter female receptacle cross section with a larger aperture and retention area to secure the male feature.

BRIEF DESCRIPTION OF THE DRAWINGS

The foregoing and other aspects, objects, features and advantages of the invention will become better understood with reference to the following description, appended claims, and accompanying drawings, where:

FIG. 1D is a front view of the surgical clip of FIG. 1A.

FIG. 2 is a close-up view of an exemplary tip of a surgical clip in a locked configuration according to principles of the invention.

FIG. 5 provides schematics conceptually illustrating various exemplary surgical clip configurations according to principles of the invention.

FIG. 6A is a detailed top view of the head mating element of the surgical clip of FIG. 1A.

FIG. 6F is a side view of a clip arm with the alternative head mating element of FIG. 6D in a first configuration.

FIG. 6G is a side view of a clip arm with the alternative head mating element of FIG. 6D in a second configuration.

FIG. 17 is a side perspective view of the clamping features of FIG. 16;

FIG. 18 is a side perspective view of the clamping features of one arm of FIG. 16;

FIG. 21B is a side perspective view of a surgical clip of FIG. 21A;

Figure 1A:
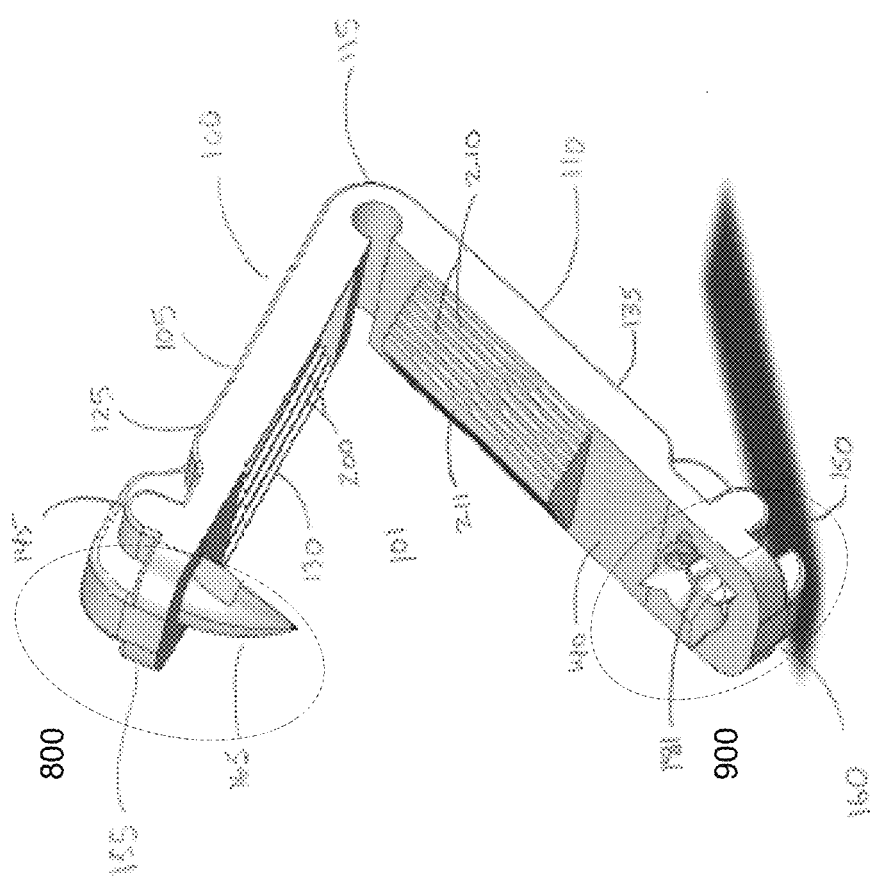
FIG. 1A is a side perspective view of an exemplary surgical clip according to principles of the invention.
Figure 1B:
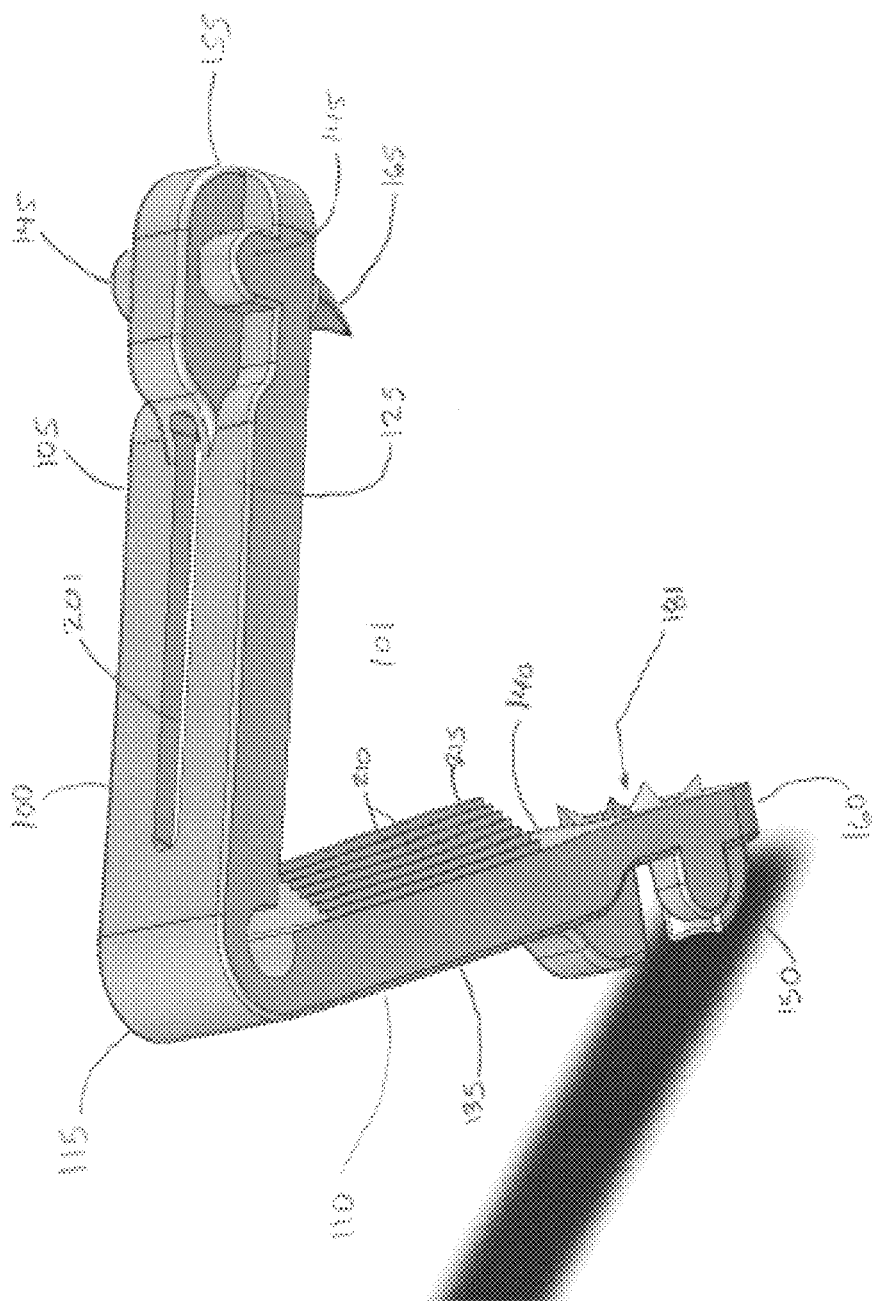
FIG. 1B is a top perspective view of the surgical clip of FIG. 1A.
Figure 1C:
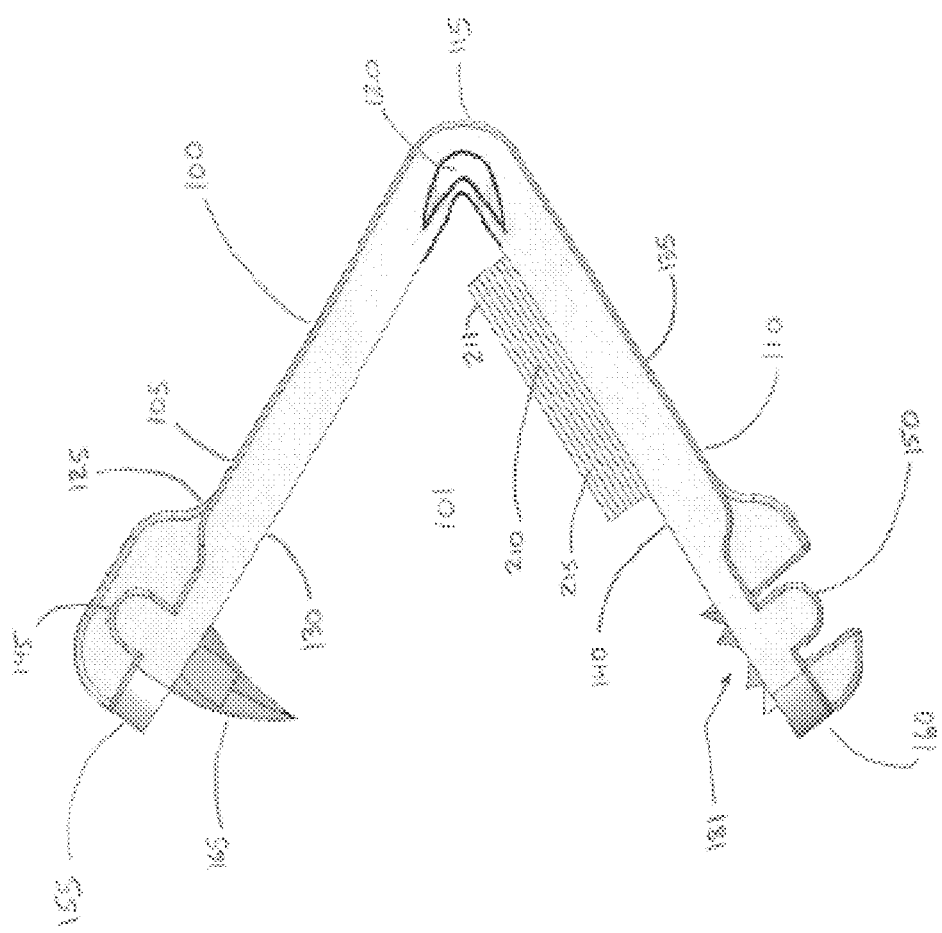
FIG. 1C is a side view of the surgical clip of FIG. 1A.

Those skilled in the art will appreciate that the figures are not intended to be drawn to any particular scale; nor are the figures intended to illustrate every embodiment of the invention. The invention is not limited to the exemplary embodiments depicted in the figures or the configuration, shapes, relative sizes, ornamental aspects or proportions shown in the figures.

DETAILED DESCRIPTION

In one embodiment, ligating clips comprise a tissue-penetrating locking mechanism with an elongated receptacle, a configuration of slip-resisting grooves on the clamping surfaces, and a hinge lock.

Clip Arms

With reference to FIGS. 1A through 3, in one embodiment, a clip 100 according to principles of the invention generally includes a pair of clamping arms 105 and 110, adjoined at an integral flexible hinged joint 115 (the "hinge"), free at the other end 155, 160 and defining an opening 101 therebetween, such as an opening having a generally u- or v-shaped space. The opening 101 is preferably sufficiently wide to engage a vessel, organ or tissue to be ligated. In the exemplary embodiment shown in FIGS. 1A, 1B, 1C, the clamping arms 105, 110 are generally rigid. However, the hinged end 115 is sufficiently flexible so that the arms, 105, 110 can be angularly deflected bringing their free ends 155, 160 towards each other to decrease the space between the arms 105, 110, until locking engagement is achieved. In the exemplary clip 100 of FIG. 1C, one or more cutouts 120 formed in the hinge 115 facilitates bending at the hinge 115. Alternatively, other configurations with a reduced cross-sectional area at the hinge 115 (e.g., an integrally formed living hinge) may be utilized to facilitate such bending while maintaining structural integrity. Because a clip 100 according to the invention is inserted into a body cavity in a fully opened configuration, the hinge is not required to facilitate expansion.

A first clamping arm 105 extends from the hinge 115. The first clamping arm 105 includes an outer side 125 and a clamping side 130.

Clamping Features

Figure 3:
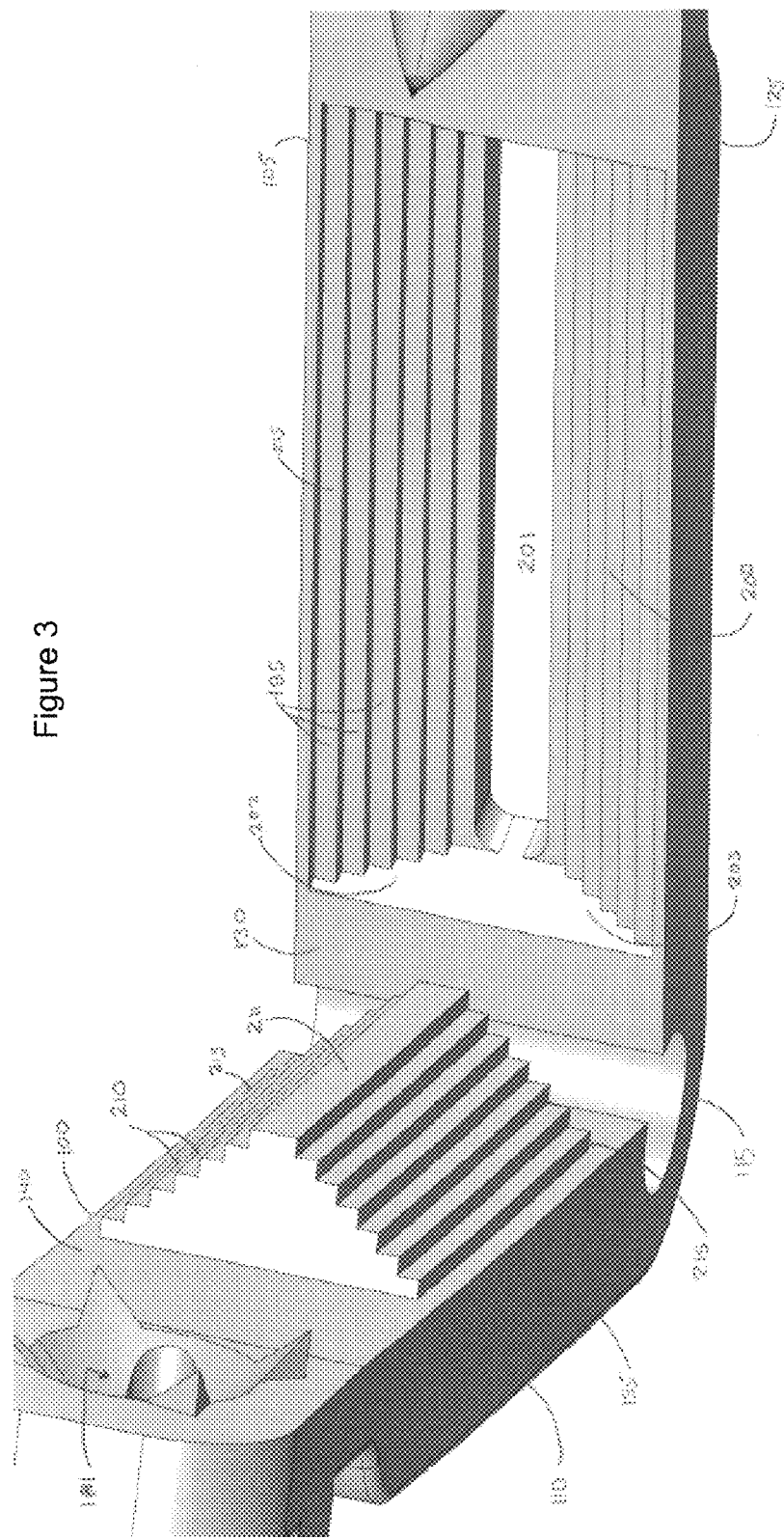
FIG. 3 is a perspective view of the step clamp features of the surgical clip of FIG. 1A.

In one embodiment, first arm 105 has a convex stepdown-like clamping side 130 and a concave or flat outer side 125. In one example, the 130 includes a configuration resembling "downward" steps to create a V-shaped trough portion 200 with an opening 201. Converging downward staircase surfaces 200 form a trough or opening 201 in the arm of the first clamping arm 105. As shown in FIG. 3, a plurality of step-like intrusions such as downward steps or ribs 185 are spaced longitudinally apart along a portion of the length of the clamping side 130 of clamping arm 105. In this example, a tissue slippage prevention feature is comprised of a zig-zag pattern that interlocks into the adjacent arm. This zig-zag pattern on cross-section resembles the steps of a pyramid; consisting of acute, orthogonal or obtuse angles creating a step-like staircase feature. The zig-zag pattern itself can also have acute, orthogonal or obtuse angles or a combination there of. A boss 145 is provided to facilitate handling and manipulation. A male pin 165 extends from the clamping surface of the first clamping arm 105.

A second clamping arm 110 includes an outer side 135 and a clamping side 140. Second arm 110 has a concave clamping side 140 and a convex or flat outer side 135. The clamping side 140 includes a triangle-shaped step-like wedge configuration resembling a pyramid 210, such as the triangle-shaped pyramid wedge conceptually illustrated in FIGS. 1A, 1B, 1C, and 3. Converging step-like staircase (i.e., angled) surfaces 215 form the an apex of the pyramid 211. The surfaces 215 converge at an apex 211 (i.e., a point of intersection). Concave clamping side 140 of second arm 110 and convex clamping side 130 of first arm 105 have substantially matching radii of curvature. The trough 200 forms a female receptacle for at least partially receiving the pyramid-like wedge 210 when the arms 105, 110 are urged together. A plurality of protrusions such as protruding rows of benches or ribs 215 are spaced apart along a portion of the length of the clamping side 140 of clamping arm 110. A boss 145, 150 is provided to facilitate handling and manipulation. A female receptacle 181 is formed in the clamping surface 140 of the second clamping arm 110.

The embodiment in FIG. 3 includes a prominent wedge or ridge 210 (e.g., an elongated ridge having a staircase-like triangle pyramid figured cross section) extending from the clamping surface of one arm 110. The surface of the prominent wedge 210 is textured with step-like protrusions 215. For example, a plurality of striations, ribs or other protuberances 215 may be provided to enhance frictional gripping force exerted by the clip 100. A corresponding trough 200 or aperture is provided on the other arm 105. The trough 200 may extend from the clamping side of the arm through the opposite side of the arm, or only partly through the arm. The trough 200 may have a shape that generally corresponds to the shape of the ridge 210. Thus, the ridge 210 mates with the trough 200 when the clip 100 is closed. End portions 202 and 203 of the clamping arm flank and define the trough 201. The tissue contacting surfaces of these portions may also be textured, e.g., feature a plurality of striations, ribs, or other protuberances to enhance frictional gripping force exerted by the clip 100. The wedge 210 and top ridge 211 mates with the trough 200 and window 201 when the clip is closed. The surface of the trough may also be textured. For example, a plurality of striations, ribs or other protuberances may be provided to enhance frictional gripping force exerted by the clip 100. The corresponding surface of one arm 105 has an open space 201 to allow bulky tissue to fill the window 201 without causing the arms 105 and 110 to bow outward when the clip is in the closed configuration around tissue.

The arrangement and configuration of the wedge and trough may vary within the scope of the invention. For example, the pyramid-like wedge 210 may be formed on the first clamping arm 105 and the step-down staircase trough 200 may be formed on the other arm 110. In this configuration, the pyramid-like wedge 210 may enhance structural integrity and stability of the first arm 105, which may facilitate closure.

Tissue Capture

The alternating staircase pattern within the inner aspect of the male and female arms acts to capture tissue into the arms of the clip as it closes rather than pushing tissue out as the clip closes. The inner teeth or jaws of the clip act as cogs or teeth where the teeth from one arm (such as the male arm of the clip) fits into a corresponding slot within the other arm (such as the female arm). Each slot is configured by the walls of two adjacent teeth. The inner teeth or the alternative staircase pattern of one clip arm (either the male or female arm) fits into a corresponding slot located on the opposite clip arm (either the female or male arm), so that the teeth from the two arms come together as a "zipper" as the clip closes. As the clip arms are re-approximated, the teeth anchor onto tissue to capture the tissue within the clip arms as it closes rather than pushing the tissue out as the clip closes.

The slot on one clip arm is a space that fits the teeth from the opposite clip arm; it is created by two adjacent teeth walls. The teeth from one arm (such as the male arm of the clip) fits into a corresponding slot or space within the other arm (such as the female arm of the clip). The teeth from one arm (such as the female arm of the clip) fits into a corresponding slot or space within the other arm (such as the male arm of the clip).

The two interacting surfaces of the clip is similar to a gear or cogwheel mechanism where the teeth or tongues (created by the alternating staircase pattern on the inner part of the clip arms) mesh together with another toothed part in order to transmit a force towards the hinge region of the clip, causing the tissue to be captured into the clip rather than outwards and away from the clip as the clip closes. There is a mechanical advantage through this gear mechanism of the alternating staircase patterned teeth on one side of the clip arm which corresponds to the slots on the opposite side of the clip arm.

Hinge

Flexible hinge 115 has a continuous concave inner surface and a continuous convex outer surface. Concave inner surface of hinge section 115 joins concave clamping side 130 of first arm 105 and convex clamping side 140 of second arm 110. Convex outer surface of the hinge 115 joins outer side 125 of first arm 105 and outer side 135 of second arm 110.

Non-Slip Features

In this embodiment, the clamping arms are configured with non-slip protrusions, such as teeth, ribs or step-like ridges. The teeth, ribs, or step-like ridges are uniquely dimensioned and configured to frictionally engage a vessel, organ or tissue. The teeth, ribs or step-like ridges protrude from the clamping-side surface of one clamping arm. The teeth, ribs or step-like ridges or protrusions increase the clamping side pressure and surface area in frictional contact with the engaged vessel, organ or tissue. In the exemplary embodiment, step-like ridges or protrusions extend along the longitudinal axis of the clamping-side surface of one arm. In one example, the height of each layer or step-like ridge of the pyramid may preferably be approximately 0.01 to 0.5 mm. A substantially greater height prevents an engaged vessel, organ or tissue from contacting the clamping side surfaces of the clamping arms between the step-like pyramid upward wedge and the step-like downward trough, thereby substantially compromising the frictionally engaging surface area. In such a case, the vessel, organ or tissue would be suspended between adjacent step-like ridges. A substantially greater height will also result in a substantially thicker clamp, which can compromise utility in endoscopic procedures.

Alternative Clamping Surfaces

Figure 4:
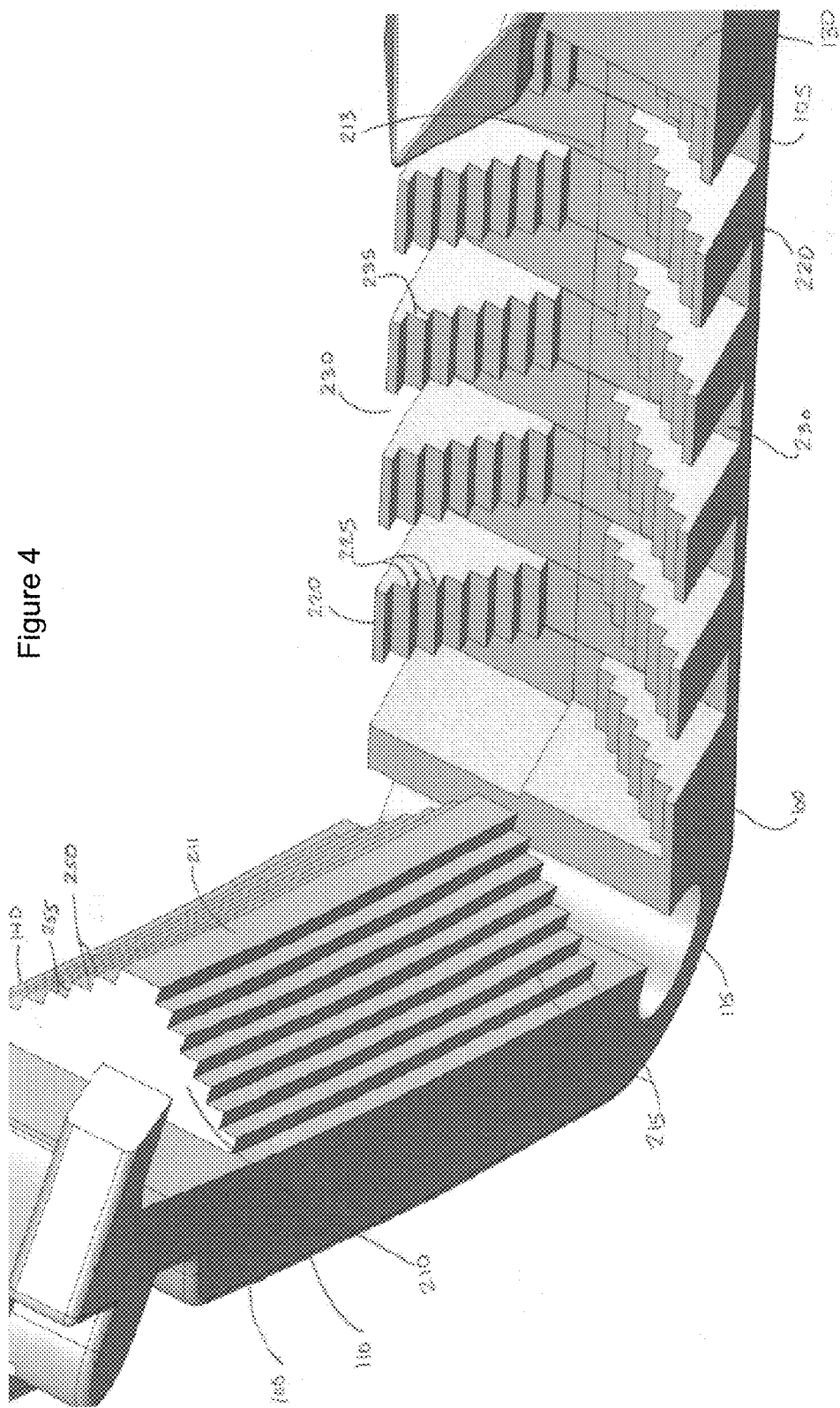
FIG. 4 is a perspective view of another embodiment of a surgical clip with spaced apart step clamp features.

Referring now to FIG. 4, portions of arms 105, 110 featuring an alternative configuration of clamping surfaces is shown. A plurality of spaced apart step-like "staircase" pillars protruding 220 from the clamping side surface 130 of the first clamping arm 105. Spaces 230 are provided between adjacent "staircase" pillars 220. Each staircase-shaped pillar protrusion 220 is comprised of chamfered (i.e., right-angled) surfaces 235 that converge at a vertex 225. Correspondingly, a wedge shaped from a step-like pattern resembling a pyramid 210 protrude from the clamping surface 140 of the second clamping arm 110. The pyramid-shaped wedge protrusion 210 is comprised of chamfered (i.e., right-angled) surfaces 255 that converge at a vertex 250. The staircase-like pillars 220 are aligned with the pyramid-shaped wedge segments 210. Thus, when the arms 105, 110 are urged together in locking configuration, the pyramid-shaped wedge 210 receives corresponding staircase-like pillar protrusions 220. When the arms are urged together to close the clip arms 105, 100, the apex of the pyramid-shaped wedge 211 will be approximated to the floor or trough 213 of the other arm 105. This configuration increases the pressure applied to vessels, organs or tissue sandwiched between the triangle-shaped pyramid-like wedge 210 and the corresponding staircase-shaped pillar protrusions 220.

In yet another alternative embodiment, the protrusions are of a size, shape and arrangement so that the protrusions of opposing arms interdigitate with one another when the opposing arms are moved toward one another. By interdigitate it is meant that the protrusions of one arm extend into spaces between counterpart protrusions of the other arm when the arms are moved towards one another. Once the arms are brought together, vessels, organ or other tissue engaged between the arms will be forced under clamping pressure to wind around the protrusions and into the interdigital spaces.

The displacement into the interdigital spaces increases the traction and gripping force of the arms upon the engaged vessel, organ or tissue and increases the force required to move the gripped vessel, organ or tissue relative to the arms. In addition, protrusions having gripping features (e.g., ribs) provide additional traction and further resist movement of the gripped vessel, organ or tissue in directions transverse to the gripping edges.

Arm Shape

The shapes of the arms may vary from straight to concave or convex. Referring now to FIG. 5, a configuration 300 with a substantially straight arm 310 and a corresponding curved (i.e., convex) arm 305 is shown. Another embodiment 400 with a pair of curved (i.e., convex) arms 405, 410 is shown. In yet another embodiment 500 a configuration with a pair of substantially straight arms 505, 510 is shown. Another embodiment 600 includes a pair of curved (i.e., convex) arms 605, 610, and a severable hinge 615. In that embodiment, the hinge 615 extends from the converging ends of the arms 605, 610. These and other arm configurations that allow clamping of vessels, organs or tissue between the arms are feasible and come within the spirit and scope of the invention. Thus, two concave surfaces may define a lens shaped space therebetween. A concave and convex surface may define a lune shaped space therebetween. Crescent, circular segment and triangular shapes may also be defined using various combinations of curved and straight arms.

Tissue Spreading Head and Head Mating Element

Figure 6B:
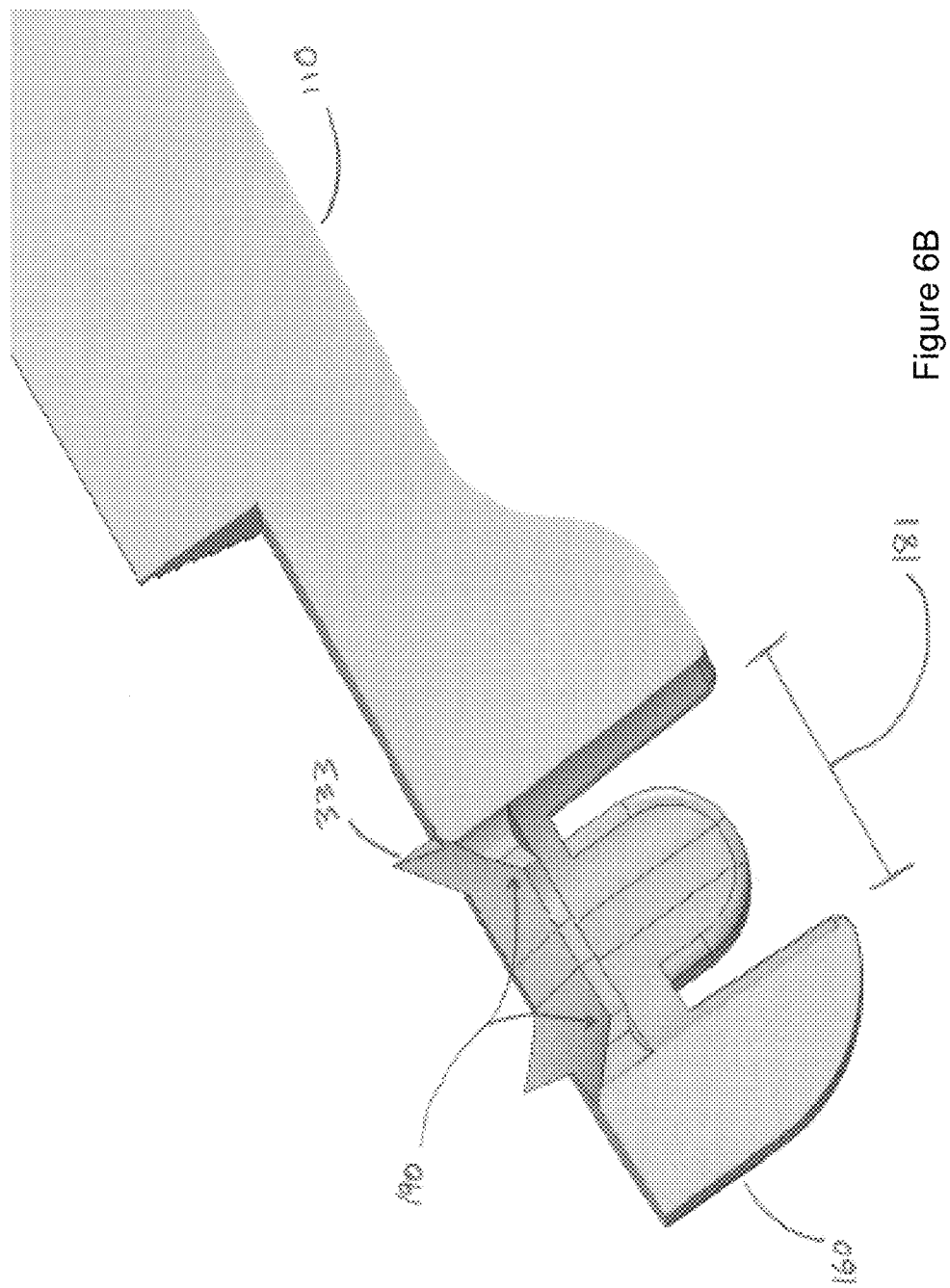
FIG. 6B is a side cross section view of the head mating element of FIG. 1A.
Figure 6C:
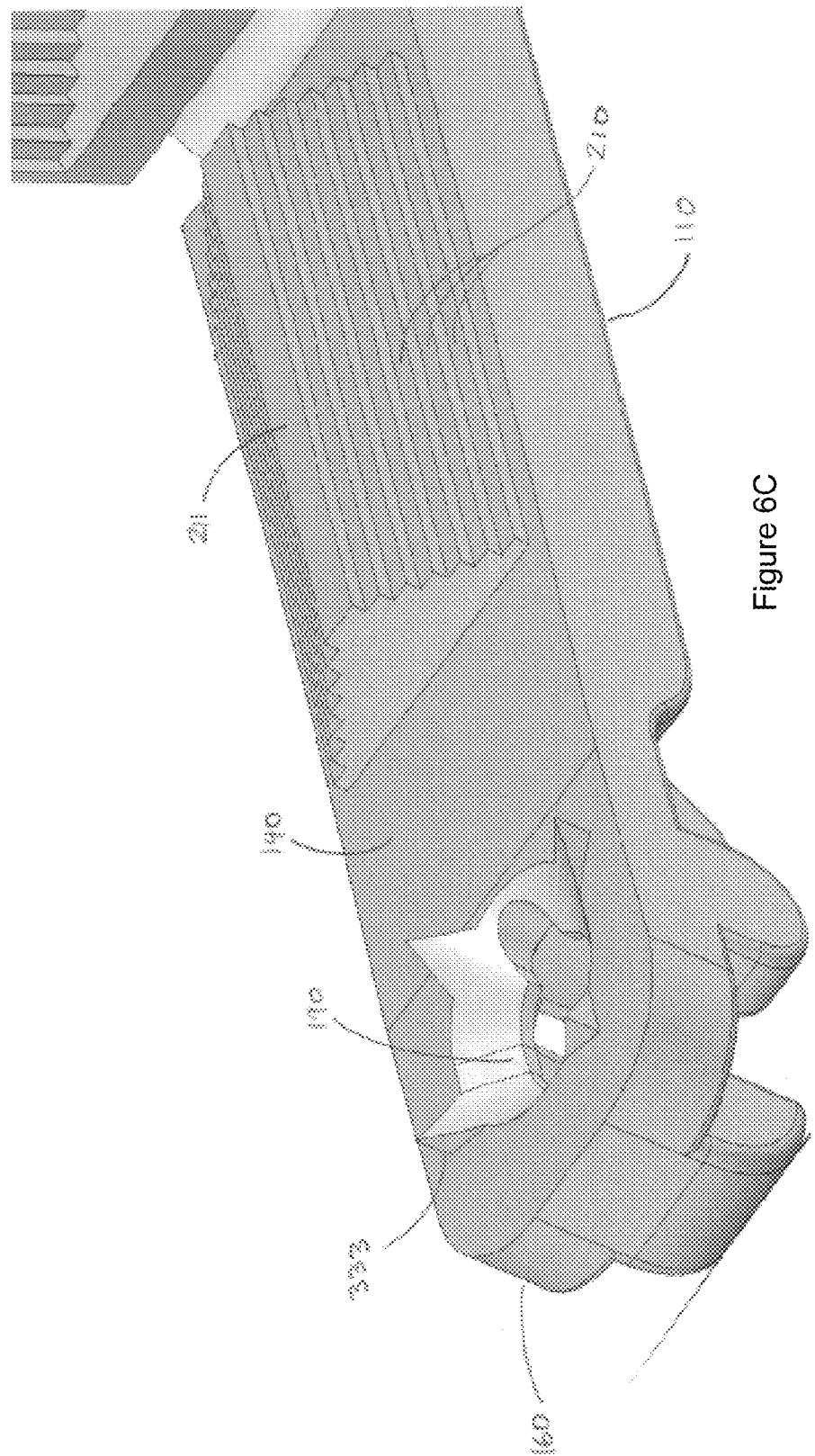
FIG. 6C is a top perspective view of the head mating element of FIG. 1A.
Figure 6D:
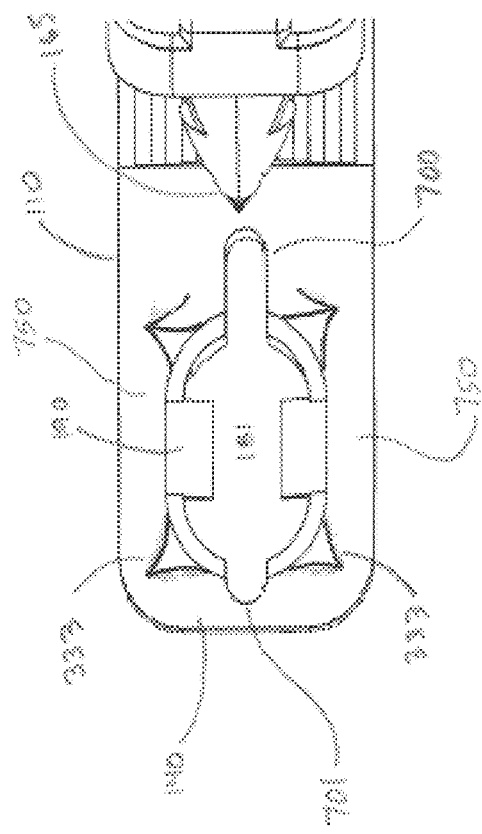
FIG. 6D is a detailed top view of an alternative head mating element of the surgical clip of FIG. 1A.
Figure 6E:
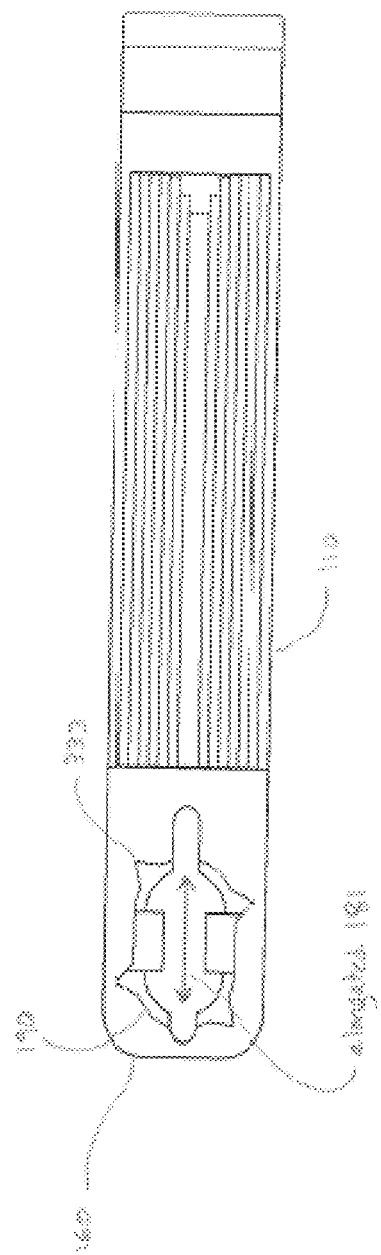
FIG. 6E is a top view of a clip arm with the alternative head mating element of FIG. 6D.
Figure 6H:
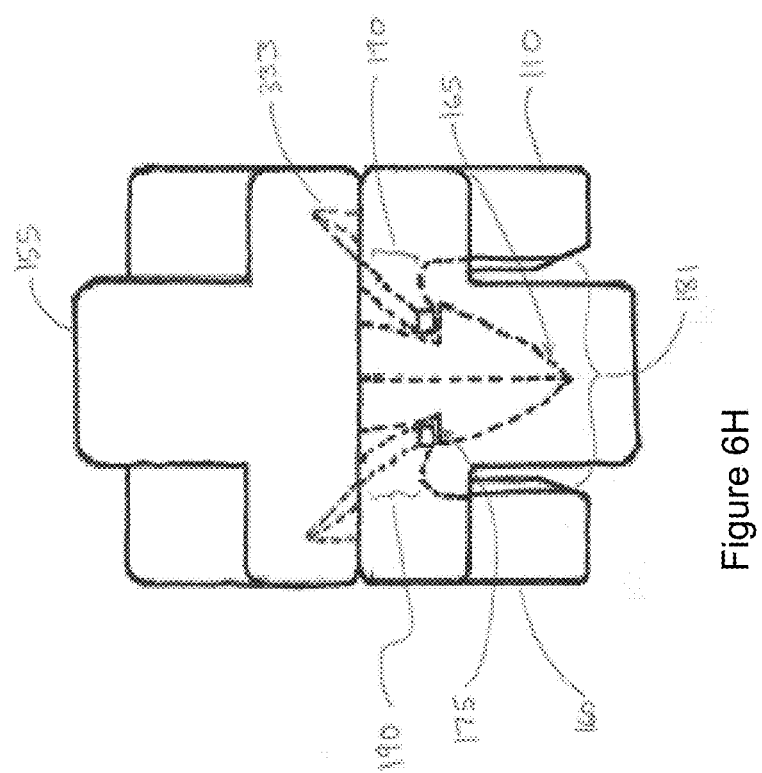
FIG. 6H is a front view of a clip arm with the alternative head mating element of FIG. 6D with the clip in a closed configuration.
Figure 7:
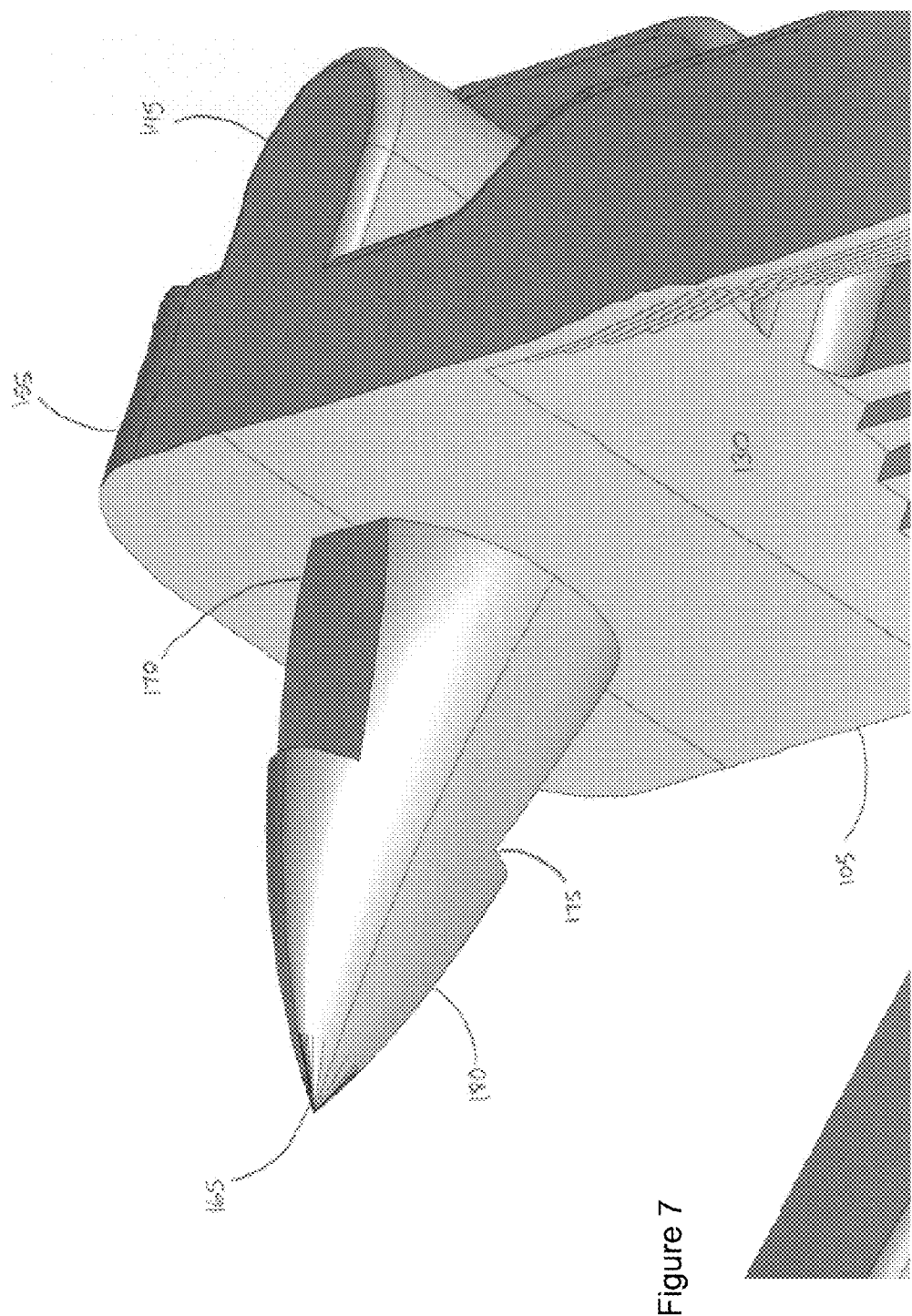
FIG. 7 is an oblique view of an exemplary male pin of a locking mechanism for an exemplary surgical clip according to principles of the invention.

Referring now to FIGS. 6 and 7, a clip according to principles of the invention includes a male and female locking mechanism, wherein the male component consists of a pin 165 configured to penetrate an engaged tissue or organ. As shown in FIGS. 6A-6G, the female receptacle 181 comprises a resilient aperture in the second arm 110, aligned with the male pin 165. A tapered section 190, flexible tab or other snap fit feature in the receptacle 181 resists withdrawal of the fully inserted male pin 165. As depicted in FIG. 6H, the two tapered sections 190 within the receptacle 181 creates a "tunnel-shaped" latch feature which locks the male pin 165 into the receptacle once the shank 175 engages the tapered tab/section 190. As shown in FIG. 7, the male pin 165 includes a base 170 which extends from the first arm 105, a shank 175 that extends from the base 170, and a head 180 that extends from the shank 175.

Elongated Aperture

In FIG. 6D, an alternative design of the female aperture, there exists two elongated troughs 700, 701 associated with the aperture 181, creating two parallel borders outlining the aperture laterally This variant of the aperture allows the lateral borders of the aperture 750 to bow outwards when the male pin 165 is urged into the female aperture 181 during closure of the clip 100. As the shank 175 of the male head of the pin 180 enters the aperture 181, it will make contact with a flexible one-way tab 190; during this process of closure, the lateral borders of the aperture 750 will bow outwards to accommodate the shank 175 and then spring inward to its original configuration as the shank 175 passes by the one-way flexible tabs 190. This will create a one-way valve to prevent the clip 100 from opening once in the closed and locked position around tissue as depicted in FIG. 6G. The two tapered sections 190 within the receptacle 181 creates a "tunnel-shaped" latch feature which locks the male pin 165 into the receptacle once the shank 175 engages the tapered tab/section 190.

In FIGS. 6E and 6F, the aperture 181 on the female receptacle 160 is designed in an elongated/oval shape to allow the male pin 165 to sit securely when clamping various thicknesses of tissue. When thick tissue is clamped between the arms 105, 110 of the clip, the two arms will bow outward, causing the male and female ends 155, 160 to fit insecurely under intense strain—predisposing it to not close securely or "pop-open" once it is clamped closed. Since the female aperture 181 is oval-shaped, the male pin 165 can fit into the female receptacle 160 securely when clamping thick tissue; the oblong/oval female aperture 181 accommodates the male pin 165 to slide within the receptacle 160 to allow the bowing of the clip arms 105, 110 without strain or tension on the male-female engagement. FIG. 6F depicts the mechanics of the male pin 165 moving proximally within the aperture 181 of the female receptacle 160 when thick tissue is clamped within the space 101 between the two arms 105, 110 of the clip.

As shown in FIG. 7, the head 180 includes a sharpened and/or pointed leading edge 165 suitable for penetrating an engaged portion of an organ or tissue. The head may be rigid biocompatible plastic, reinforced biocompatible plastic, or biocompatible metal.

The head 180 is configured to pass through the opening in the female receptacle 181, yet resist withdrawal. The head 180, the female receptacle 181 or both may exhibit resiliency to allow passage of the head for locking. The bulbous portion, arrow-shape, flanged edge, detents or cone-shape of the head resist or prevent withdrawal of the head after it has been urged through the female aperture.

Clip Alignment Guides

Figures 19A, 19B:
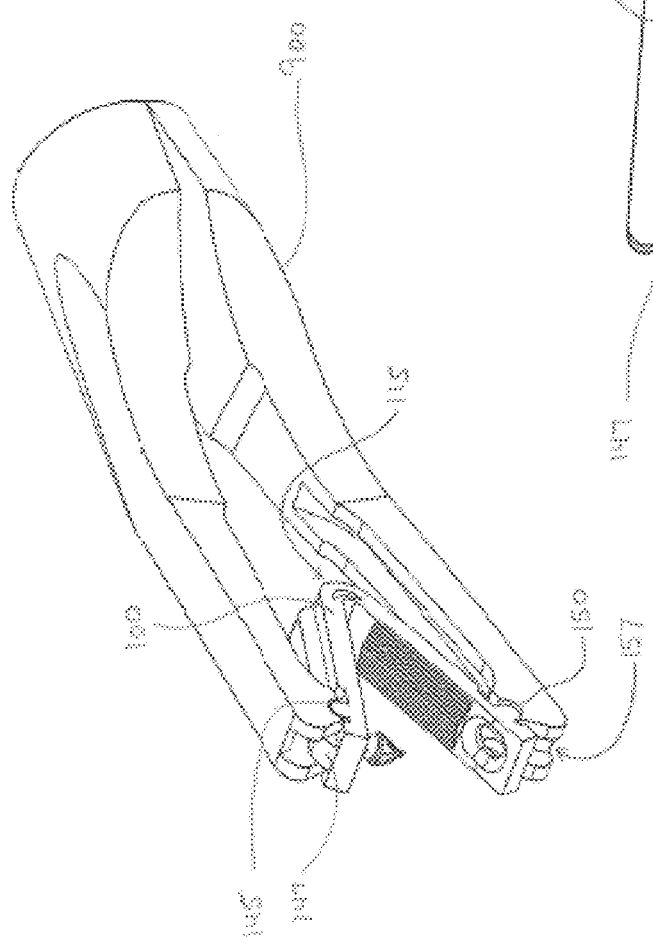
FIG. 19A is a side perspective view of a surgical clip positioned in the tip of an applicator.
FIG. 19B is a side view of the surgical clip of FIG. 19A positioned in the tip of an applicator.

Adjacent to the distal (free) ends of the first and second arms and adjacent to the male pin 165 and female aperture 181, a pair of cylindrical bosses 145, 150 are formed coaxially on the opposed lateral surfaces of the first and second arms 105, 110. The bosses 145, 150 project outwardly beyond the outer surfaces of the arms 105, 110. An applicator engages the clip 100 using the bosses 145, 150. An alternative design of the bosses 145, 150 to prevent undesired angulation of the clip 100 during use with the applicator 900 is depicted in FIGS. 19A and 19B. Adjacent to the circular bosses 145, 150, there are rectangular-shaped alignment guides 147, 157 located on each arm 105, 110 of the clip. These rectangular-shaped alignment guides 147, 157 provide stability of the clip. Rectangular-shaped alignment guides 147, 157 maintain the alignment of the clip 100 within the arms of the applicator 900 while it is applied onto tissue, preventing the proximal end of the clip 115 (the hinge region) from angulating out of the jaws of the applicator 900. As shown in FIG. 19a, the applicator tip may engage the front portion of alignment guides 147 and 157 to prevent lateral movement of the clip. As shown in FIG. 21D, the applicator may also include fixture elements for engaging the rear portions of alignment guides 147 and 157 to retain the rear portion of the clip in alignment with the applicator tip.

Materials

Clips according to principles of the invention may be comprised, in whole or in part of metals such as stainless steel, titanium, tantalum, or alloys thereof. Bioabsorbable and radiolucent versions may be comprised of a one-piece integral polymeric body formed from a suitable strong biocompatible engineering plastic such as the type commonly used for surgical implants. Examples of suitable plastics include acetal polyoxymethylene (POM), polyethylene terephthalate (PET), polybutylene terephthalate (PBT), polyoxymethylene, polyetheretherketone (PEEK), polypropylene, and polyethylene or other thermoplastic materials having similar properties that can be injection-molded, or other thermoplastic materials having similar properties that can be injection-molded, extruded or otherwise processed into like articles.

Clip Application

In use, the clip 100 is positioned and compressed into a locked position using an applicator. In one example, an applicator includes a forceps-type applier having a conformal jaw assembly used to grip and maintain alignment of the clip during placement and compressive deformation. The proximal end of the applicator includes a handle assembly with a stationary element and a movable (e.g., pivoting) element. A linkage contained within an elongated tubular shaft operably couples the movable handle element to the conformal jaw assembly. The shaft preferably fits through a 10-15 mm trocar. The distal end of applicator generally comprises the conformal jaw assembly having opposing pivotable jaws which have respective jaw recesses adapted to engage and retain bosses 145, 150 of the clip 100. Closure of the jaws of the applicator compresses the held clip 100. This causes the first and second arms 105, 110 of the clip 100 to close around a vessel, organ or tissue with clamping sides of the first and second arms 105, 110 contacting the outer surface of the engaged vessel, organ or tissue.

Head Penetration and Lock

Figure 20B:
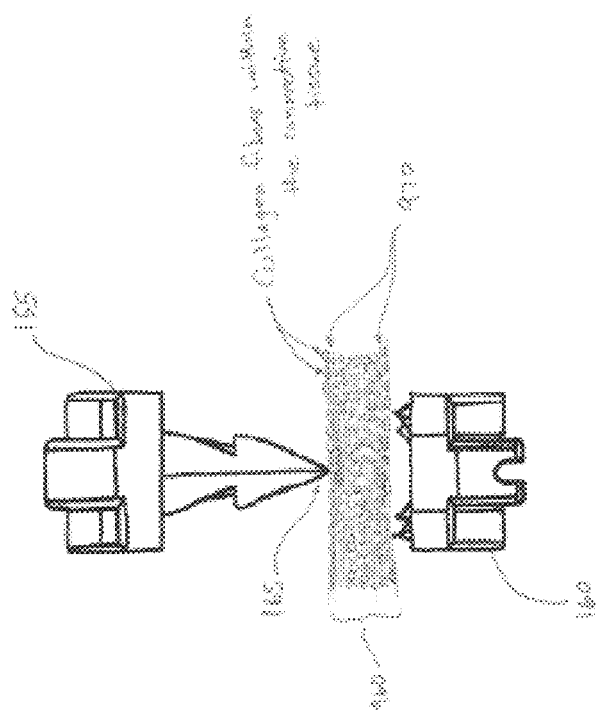
FIG. 20B-20E are front views of the surgical clip of FIG. 20A, as the clip is closed and penetrates tissue.
Figure 20A:
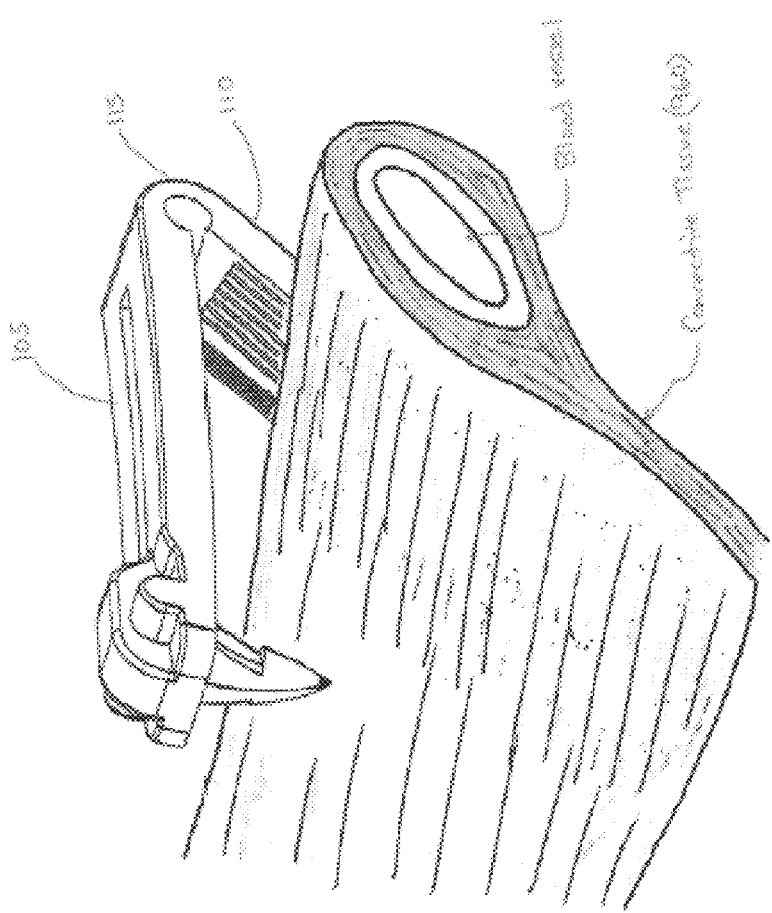
FIG. 20A is a side perspective view of a surgical clip in an open orientation positioned to clamp a blood vessel.
Figure 20C:
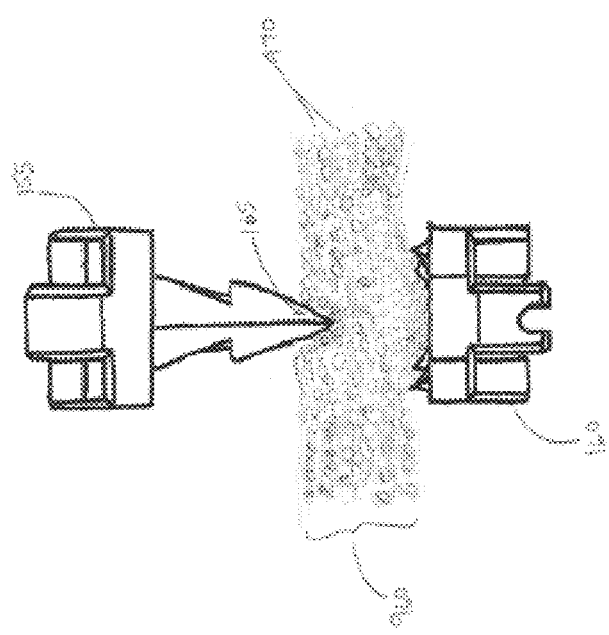
Figure 20D:
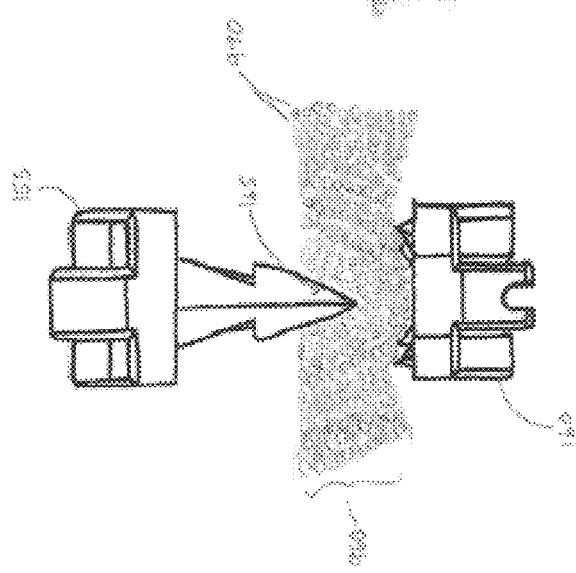
Figure 20E:
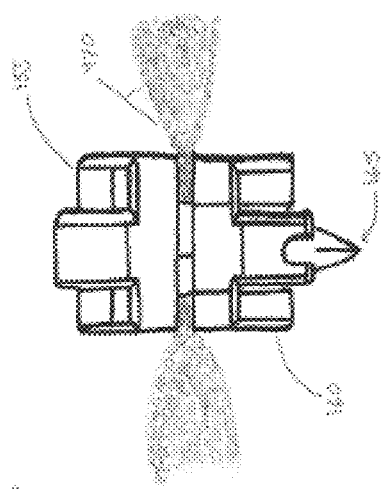

As the clip is compressed, any portion of the engaged vessel, organ or tissue or surrounding tissue in the path of the male pin will be penetrated by spreading tissue laterally as depicted in FIGS. 20A and 20B. In one invention model of the clip in FIGS. 6A, 6B, 6C, 6D and 7, as compression continues, the male pin 165 begins to contact the female aperture 181. Further pivotal movement by the applicator urges the pin into the aperture until the head of the pin 180 is forced through the aperture 181 and passes adjacent to the tapered section 190, flexible tab or other snap fit feature in the receptacle. Thereafter, the shank 175 of the male pin is matingly seated in the female aperture 181 and resting on the tapered section 190, flexible tab or other snap fit feature to resist withdrawal of the fully inserted male pin 165. This is the locked position. Upon release of the applicator instrument, the clip remains in the locked position. Once in the locked position, reference to FIGS. 2 and 11, the male pin 165 resists withdrawal from the female receptacle 181 by allowing the shank 175 to engage the tapered tab 190 or other snap fit feature in a one-way forward fashion.

As depicted in FIGS. 20A and 20B, the clip penetrates tissue by spreading the fibers of the tissue laterally or aside to allow the male pin 165 to penetrate the tissue atraumatically and without cutting into the tissue. All endovascular tissue in the human body is made of organized collagen fibers—not random placement of cells; these fibers 970 are organized layers of cells that create cylindrical-shaped fibers. These collagen fibers 970 are assembled in organized fashion to create connective tissue 960. Connective tissue 960 is the backbone of every organ and blood vessel in the human body; it surrounds organs and vessels to give it structure, shape and substance. The male pin 165 is designed to separate these organized layers of collagen fibers 970 laterally as it penetrates tissue 960.

Alternate Hinges

Figure 8A:
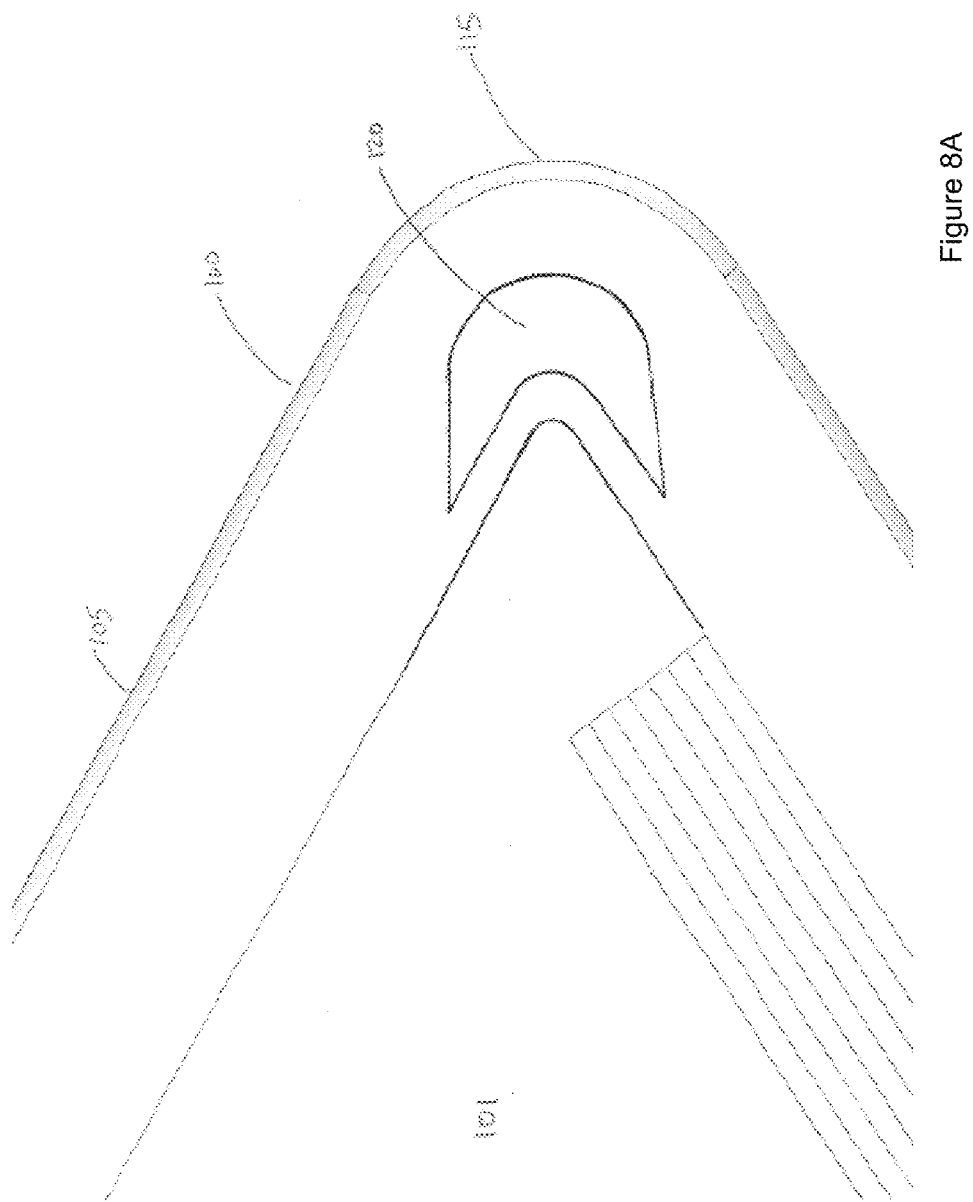
FIG. 8A is a detailed side view of the hinge portion of a surgical clip.
Figure 8C:
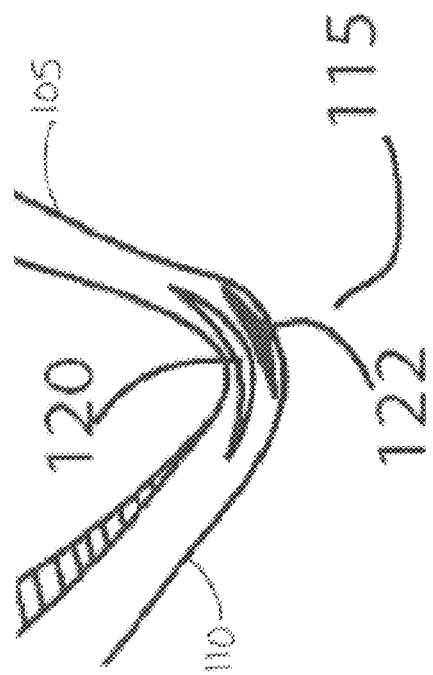
FIG. 8C is a side view of an third alternative hinge portion of a surgical clip.
Figure 8B:
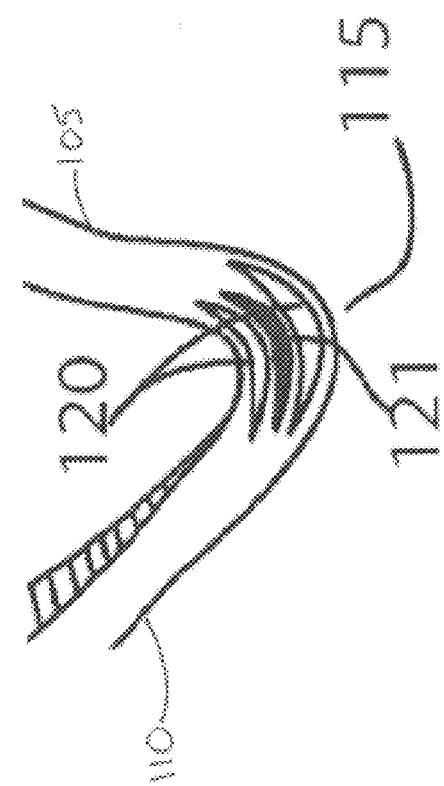
FIG. 8B is a side view of an second alternative hinge portion of a surgical clip.
Figure 8E:
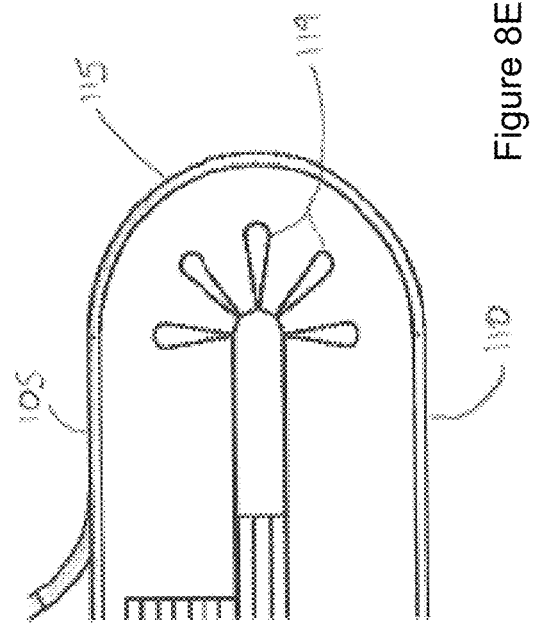
FIG. 8E is a side view of the fourth alternative hinge portion of FIG. 8D, with the hinge in a closed orientation.
Figure 8D:
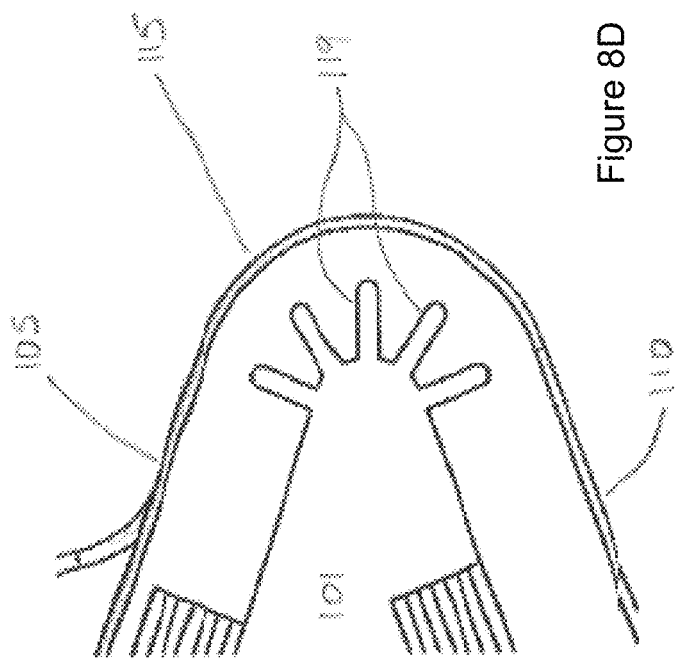
FIG. 8D is a side view of a fourth alternative hinge portion of a surgical clip, with the hinge in an open orientation.

With reference to FIGS. 8A through 8F, various exemplary embodiments of a clip 100 according to principles of the invention are illustrated. The hinged sections of the clips vary. In each case, the width and/or thickness of the hinge section 115 is equal to, less than, or greater than the average thickness of a clamping arm 105, 110. In each case the hinged section 115 includes one or more apertures 120 to facilitate bending. In FIGS. 8B and 8C, the hinged section includes a boss 121, 122 to facilitate manipulation. The boss 121, 122 (i.e., a hinge boss) is a protruding feature that can be gripped by the applicator during insertion. The shape and position of the hinge boss may vary within the scope of the invention. An alternative design of the hinge is shown in FIG. 8D; the hinge 115 resembles a star-shaped or fan-shaped configuration with multiple finger-like projections 119 radiating outwards. The radial cut-outs 119 at the hinge area 115 allows the clip 100 to accommodate various tissue thicknesses as the clip arms 105, 110 are reapproximated to each other during the clip closure process. The star-like configuration 119 of the hinge 115 allows the hinge to act as an "accordion" to accommodate various tissue thicknesses within its arms 105, 110 while maintaining ample pressure on the clamped tissue to prevent slippage under high pressures.

Hinge Lock

Figure 8G:
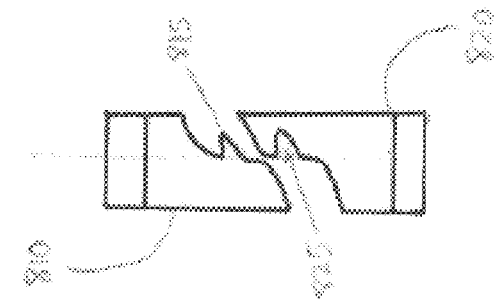
FIG. 8G is a front view of the hinge lock of FIG. 8F when a surgical clip is in an open configuration.
Figure 8H:
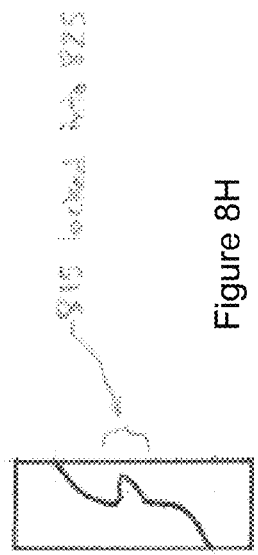
FIG. 8H is a front view of the hinge lock of FIG. 8F when a surgical clip is in a closed configuration.
Figure 8F:
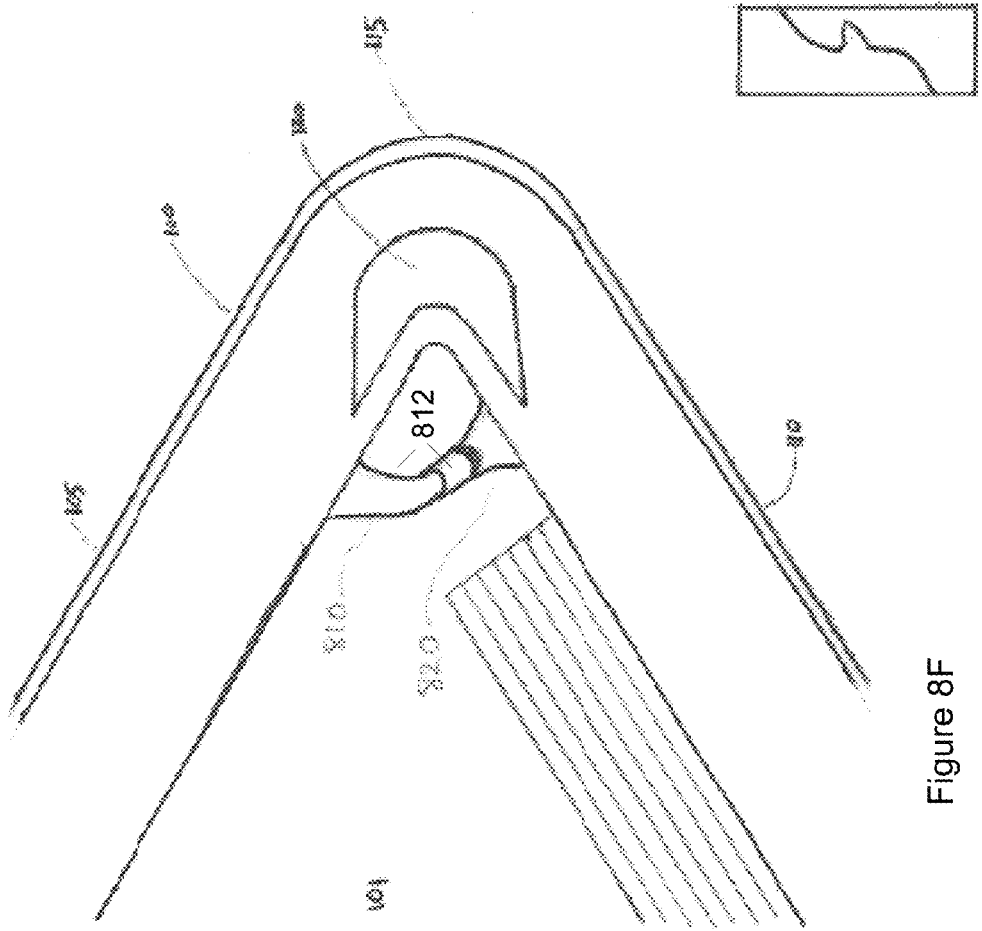
FIG. 8F is a side view of a hinge portion of a surgical clip with a first example hinge lock.

In FIGS. 8F-H, the hinge portion 115 of a surgical clip is constructed with a hinge lock 812 comprising a first hinge locking element 810 and a second hinge locking element 820, thus providing an irreversible locking mechanism at the proximal hinge end 115 of the clip 100. As the clip arms 105, 110 are re-approximated together to clamp tissue between the arms, a prong 815 of first hinge locking element 810 will fit irreversibly into a slot or groove 825 of the second hinge locking element 820. Once the prong 815 and slot 825 are united, the hinge 115 is said to be in the locked and closed position. By having a hinge lock apparatus at the hinge area, there will be constant pressure applied to the tissue being clamped at the hinge region as well as the male-female locking interface region—a parallel tension mechanism from both ends of the clip. This hinge lock, or an alternative hinge lock can be provided in combination with various head mating designs and arm clamping surfaces, such as illustrated in the example figures.

Side Hinge Lock

Figure 21A:
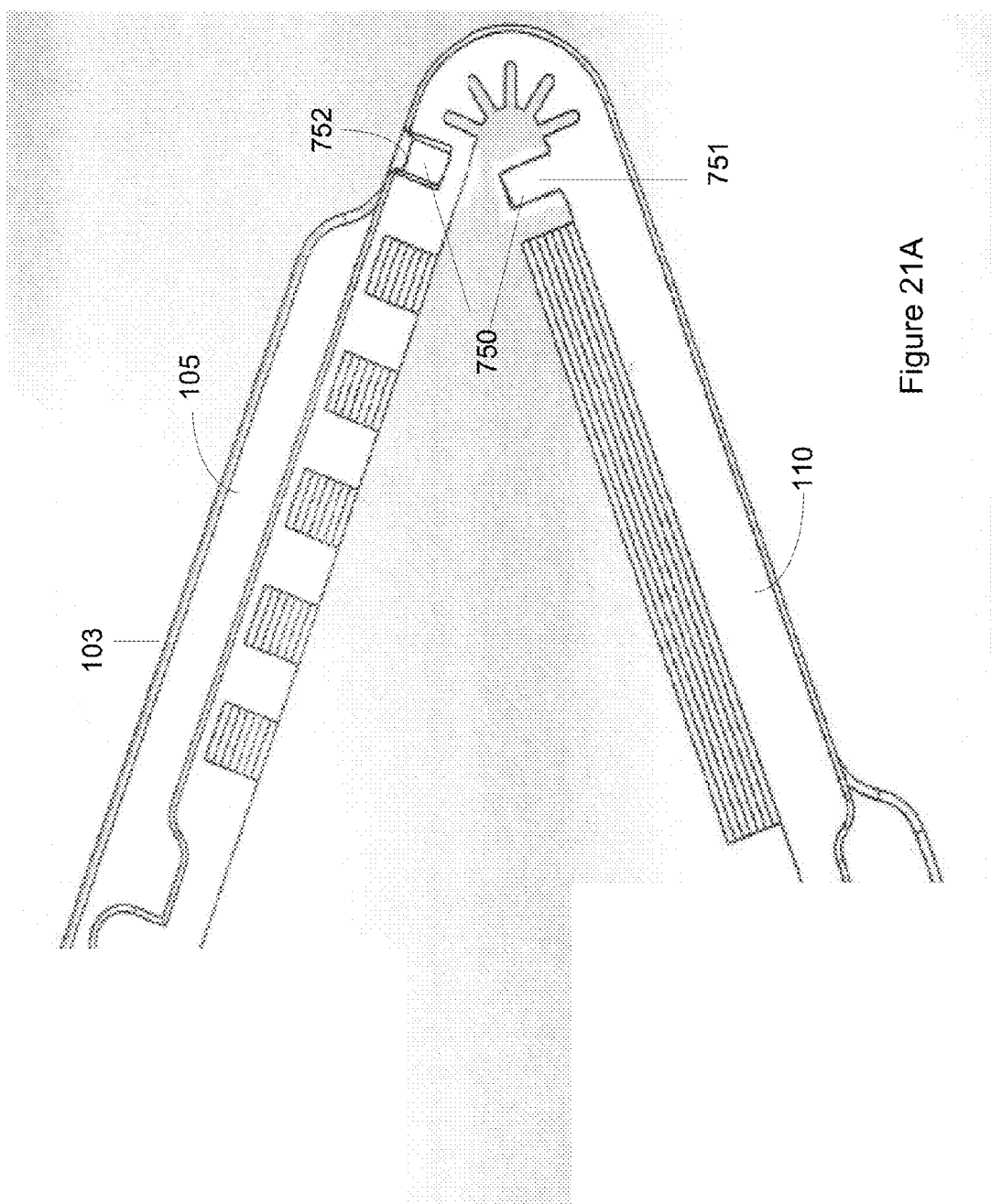
FIG. 21A is a side view of a surgical clip in an open configuration, with side hinge locks in an open configuration.

FIG. 21A is a side view of a surgical clip 103 in an open configuration, with a first side hinge lock 750 in an open configuration with latch element 751 provided on arm 110 and catch element 752 formed as a recess on arm 105. FIG. 21B is a side perspective view of a surgical clip of FIG. 21A showing a latch element 761 of second hinge lock 760 on the opposite side of arm 105 from the first side hinge lock.

Figure 21C:
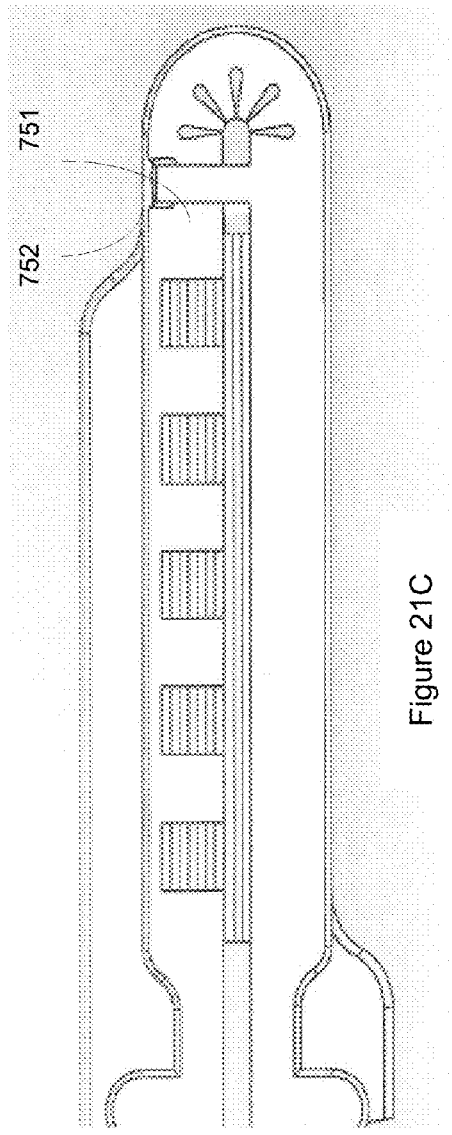
FIG. 21C is a side view of the surgical clip of FIG. 21A with the hinge locks in an engaged configuration.
Figure 21D:
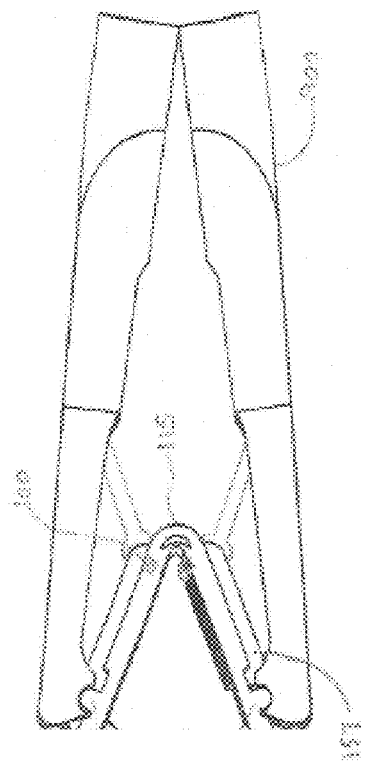
FIG. 21D is a side view of the surgical clip of FIG. 21A positioned in a clip applicator.

FIG. 21C is a side view of the surgical clip of FIG. 21A with the first side hinge lock in an engaged (locked) configuration. In this example, a first lock is provided between the male head element 800 and the head mating element 900; and a second set of locks is provided by hinge locks 750 and 760.

FIG. 21D is a side view of the surgical clip of FIG. 21A positioned in a clip applicator.

Ratcheting Hinge Lock

Figure 8J:
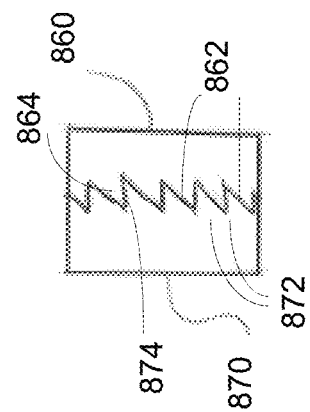
FIG. 8J is a rear view of the ratcheting hinge lock of FIG. 8I.
Figure 8I:
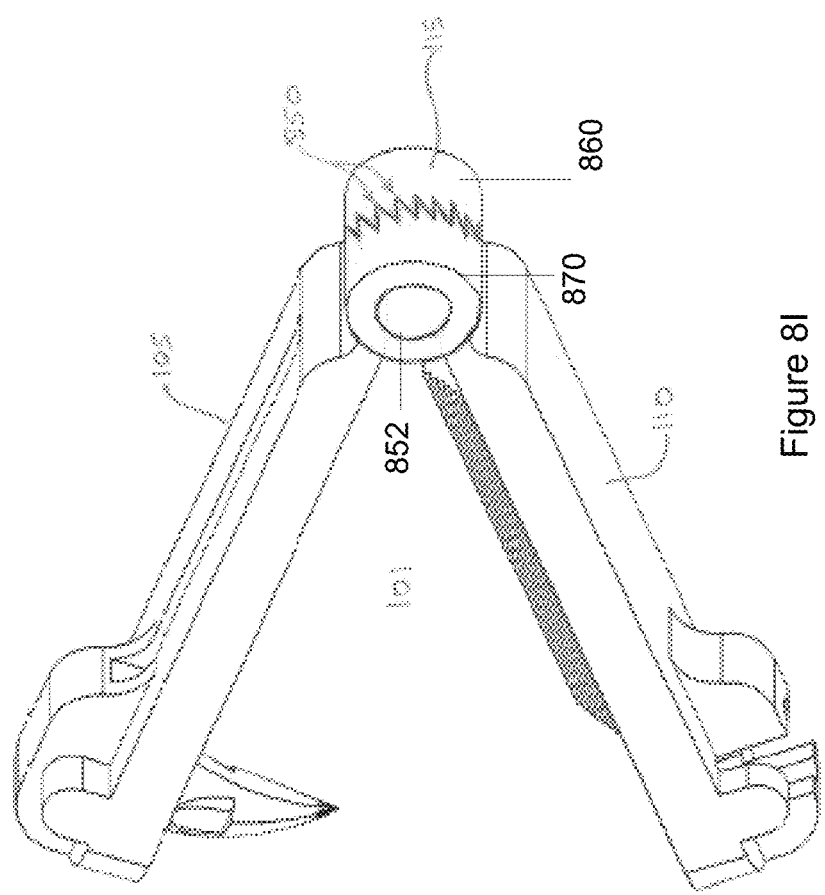
FIG. 8I is a side view of a surgical clip in an open configuration, with a ratcheting hinge lock in an open configuration.

FIG. 8I is a side view of a surgical clip in an open configuration, with an a ratcheting hinge lock 850. FIG. 8J is a rear view of the hinge lock. In this example, the ratcheting hinge lock 850 comprises a first hinge portion 860 integral to arm 105, and a second hinge portion 870 integral to arm 115. A pin 852 may be provided on either hinge portion. As arm 105 is moved toward arm 115, teeth 862 in the first hinge portion 860 rotate past teeth 872 in the second hinge portion 870. Each tooth 862 comprises a latch element 864 which engages a corresponding catch element 874 on teeth 872. The engagement of the latch element 864 by the catch element 874 prevents the arms from opening. In this example, a first lock is provided between the male head element and the head mating element; and a second lock is provided by hinge locks 850.

Bosses

Thus, the clip may include a unique arrangement of bosses. As discussed above, there may be bosses at the free end of the arms. There may also be one or more bosses, such as boss 121, 122, at or near the hinge. The applicator will hold the clip by its bosses until the clip is released from the applicator. Gripping the boss at the hinge until the clip is released provides enhanced control and stability of the clip while applying to tissue. Specifically, gripping the boss at the hinge may prevent unwanted angulation of the clip.

Clip Size

A clip according to principles of the invention can be sized to accommodate various vessels. In an exemplary embodiment, the clips are sized to work with laparoscopic procedures, meaning that it preferably can fit through a 10-15 mm trocar. It may pass through the trocar in a partially clamped state. After passing through the trocar, if the clip was partially compressed, then the jaws of the applicator and the clip will expand into a fully opened state. Thus, other than being sized for use with a laparoscopic procedure, the size of the clip may vary considerably to accommodate various vessels.

Tissue Piercing Head

Figure 10:
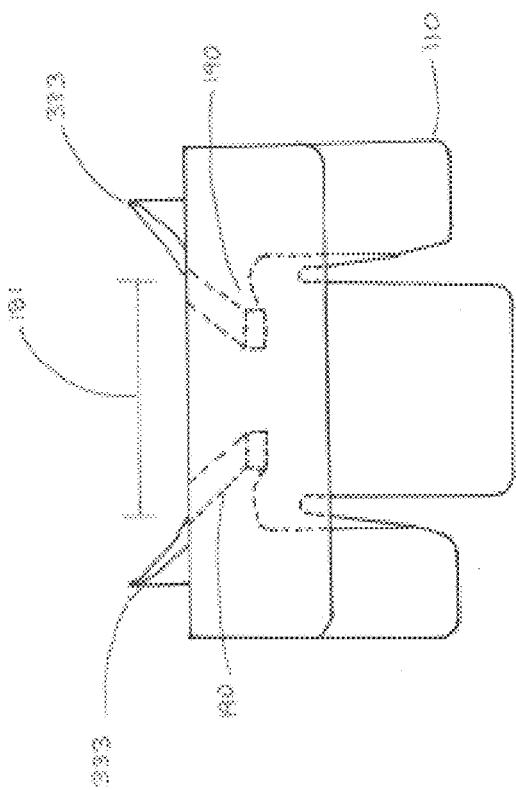
FIG. 10 is a front view of a head mating element.
Figure 9:
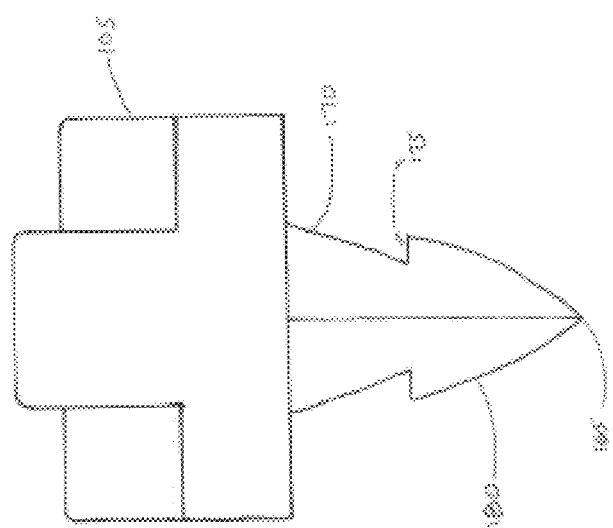
FIG. 9 is a front view of a male head element.
Figure 11:
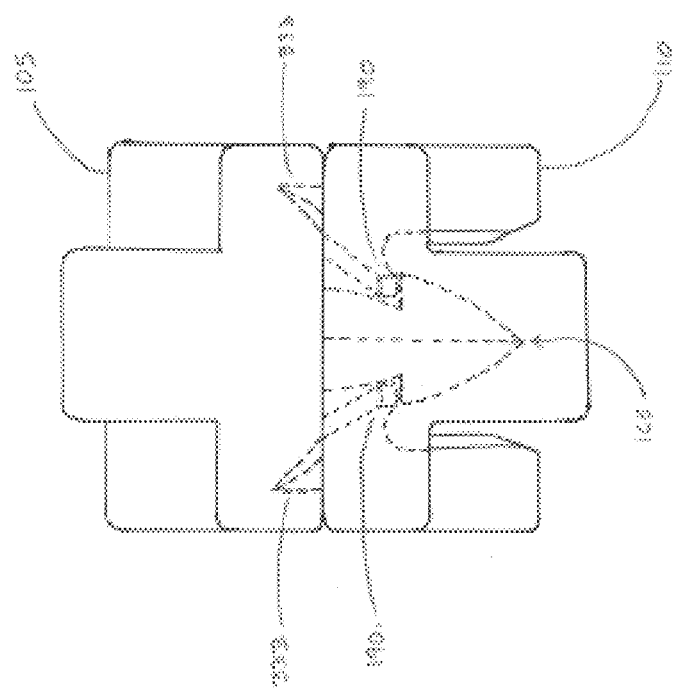
FIG. 11 is a front view of a male tip engaged by a female tip of an exemplary surgical clip according to principles of the invention.

Referring now to FIGS. 9 through 11, additional exemplary male and female locking mechanisms are illustrated, wherein the male component is an arrow-like or cone-shaped lance 180 configured to penetrate an engaged tissue or organ. The lance 180 in FIG. 9 includes a sharp tip 165 for penetrating tissue, extending outwardly from a shank 175. The shank extends from a base 170 to a sharp tip 165. The leading edge of the tip may be sharp.

As shown in FIGS. 10 and 11, the female receptacle 181 comprises an aperture near the free end of an arm 110, aligned with the male pin 180, 165. The apertures may be generally aligned with bosses 145, 150. The receptacle in FIG. 10 includes a one-way catch 190 that engages the resilient male pin 165 when the two arms 105, 100 are urged together via an applicator. A tapered section 190, flexible tab, catch or other snap fit feature in the receptacle 181 of FIG. 10 resists withdrawal of the fully inserted male pin 165, 180. The mated male lance and female receptacles are illustrated in FIGS. 2 and 11.

The female receptacle 181 is surrounded by four sharp triangular-shaped pyramid structures 333. These four sharp pyramid-shaped teeth 333 are arranged in the four quadrants surrounding the female receptacle 181. These sharp pyramid-like teeth 333 provide counter-traction of the tissue as the male pin 165 advances through the tissue and into the female aperture 181. The sharp pyramid-shaped teeth 333 enhances the tissue penetrating capability of the male pin 165 when advancing it through thick tissue. The female receptacle 181 is elliptical or oval in shape as depicted in FIG. 6A through 6D. This elliptical feature allows the male pin 165 to enter the aperture 181 at varies angles based on the amount of bulky tissue held within the two clamping arms 105, 110.

In each case, the head of the lance 180 includes a sharp and/or pointed leading edge 165 suitable for penetrating an engaged portion of an organ or tissue. The head 180 may be rigid biocompatible plastic, reinforced biocompatible plastic, or biocompatible metal. The head 180 is configured to pass through the opening in the female receptacle 181, yet resist withdrawal. The head 180, the female receptacle 181, or both may exhibit resiliency to allow passage of the head for locking. The bulbous portion, arrow-shape, flanged edge, detents or cone-shape of the head resist or prevent withdrawal of the head after it has been urged through the female aperture. The tip of the head 165 of the lance should not extend beyond the margins of the female arm 110 when the clip is closed. Thus the tissue penetrating tip will not rub against, abrade, puncture, pinch or otherwise harm adjacent structures.

Tissue Gripping

Figure 12:
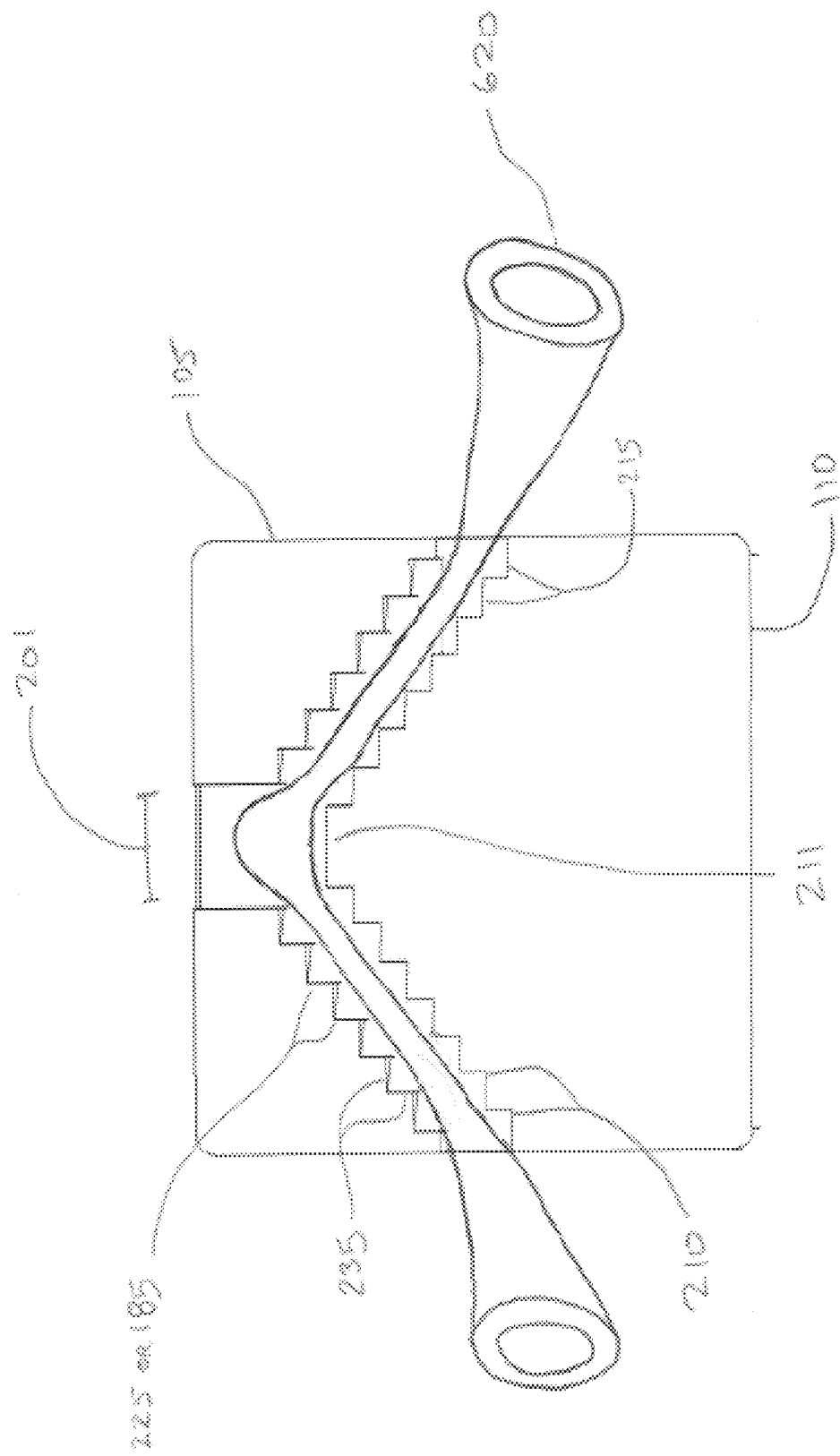
FIG. 12 is a cross-sectional front view of a portion of an exemplary surgical clip where the male arm has been engaged by a female arm.

FIG. 12 provides a cross-sectional view from the clip in FIGS. 1 and 11. As shown, tissue (i.e., tissue or a vessel, collectively "tissue") 620 is folded and sandwiched between the ridge 210 of one arm 110 and the trough 185 of the other arm 105. A substantial portion of tissue is wedged into the trough. The surface area of tissue that contacts gripping surfaces of the clamp 100 is significantly greater than in the case of a substantially planar clamping surface. The peak of the ridges 185, 215, 225, 235, 250, 255 substantially increases the frictional gripping force resisting lateral movement of the tissue. This configuration resists dislodging of the clip.

Figure 13:
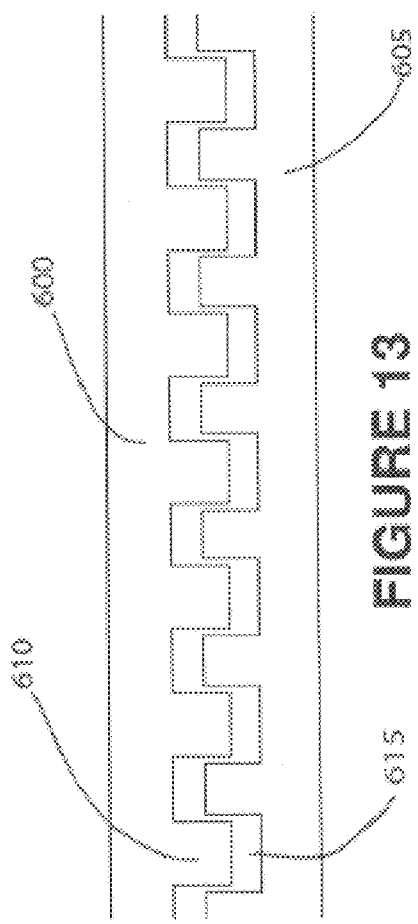
FIG. 13 is a side view cross section side view of a portion of clip arms with alternative clamping features.
Figure 14:
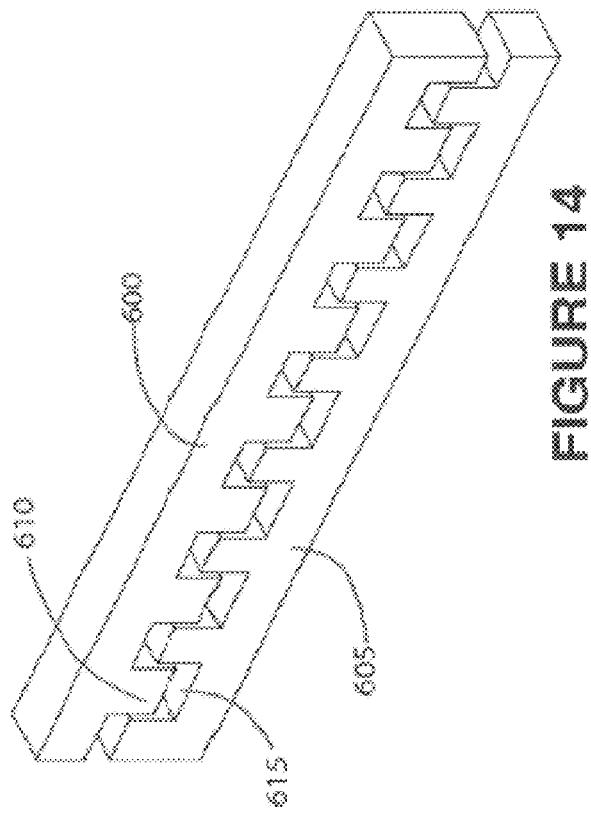
FIG. 14 is a side perspective view of the clamping features of FIG. 13.
Figure 15:
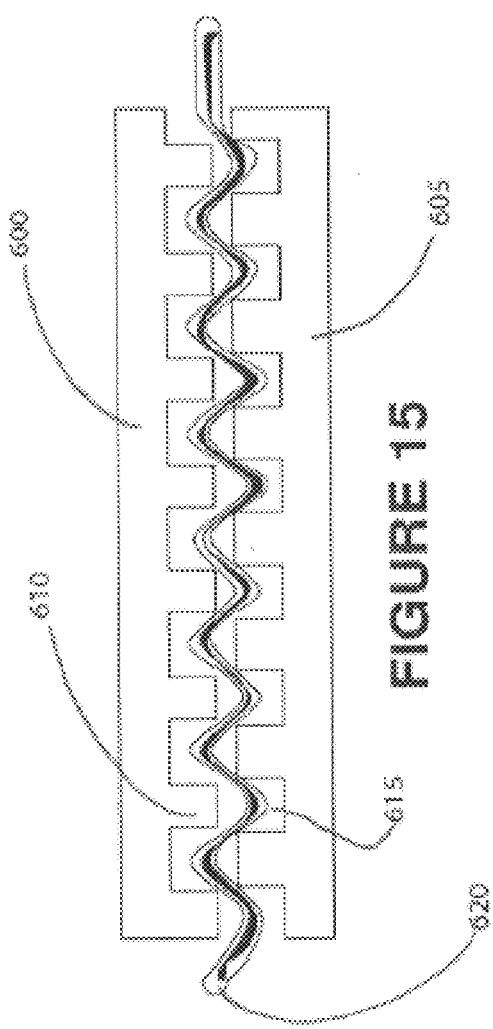
FIG. 15 is a side perspective view of the clamping features of FIG. 13 with clamped tissue.

Referring now to FIGS. 13 through 15, various views of arms 600, 605 of an exemplary surgical clip with interdigitating teeth 610 according to principles of the invention, are conceptually illustrated. Straight arms 600, 605 are illustrated. However, the invention is not limited to straight arms. Rather, curved arms may be used within the scope of the invention. While the teeth 610 are shown with a generally rectangular shape, teeth with other shapes may be used without departing from the invention. For example, the teeth may be v-shaped, u-shaped, or some other shape, or have beveled or filleted edges. The teeth fit into corresponding gaps 615 in the opposite arm. The gaps are shaped and sized to receive the teeth as well as portions of a clamped tissue or vessel 620 urged into the gaps by the teeth. The number, size and configuration of teeth and gaps on the clamping surfaces may vary without departing from the invention. The interdigitating or interfitting teeth bend the clamped tissue or vessel and provide increased surface area for frictional engagement. Counter-intuitively, a clamping surface with teeth may damage tissue less than a smooth surface because the toothed surface can grasp with less overall pressure.

Other Gripping Features

Figure 16:
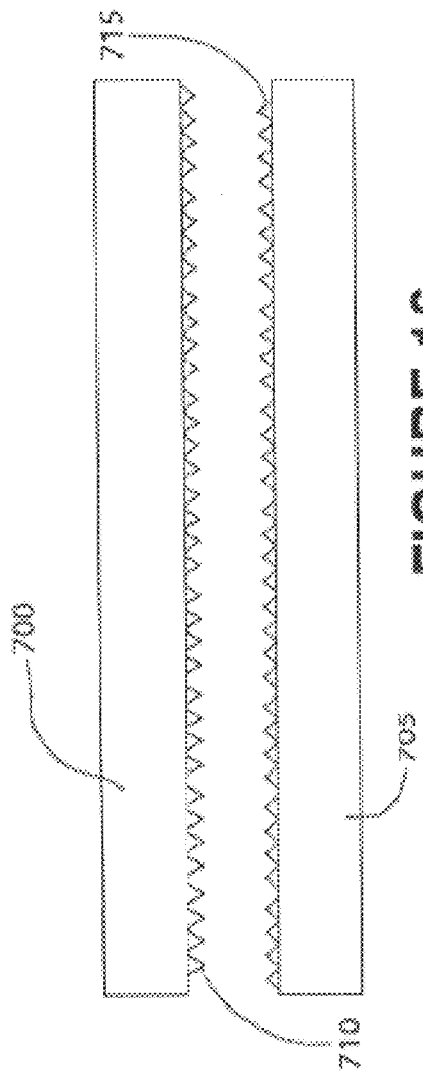
FIG. 16 is a side view cross section side view of a portion of clip arms with a plurality of teeth clamping features.

Referring now to FIGS. 16 through 18, various views of arms 700, 705 of an exemplary surgical clip with interdigitating conical teeth 710, 715 according to principles of the invention. Straight arms 700, 705 are illustrated. However, the invention is not limited to straight arms. Rather, curved arms may be used within the scope of the invention. While the teeth 710, 715 are shown with generally pointed tips, teeth with other shapes may be used without departing from the invention. For example, the tip may be slightly dulled or rounded. The teeth fit into corresponding gaps or spaces between teeth in the opposite arm. The gaps are shaped and sized to receive the teeth. In this embodiment, the tips of the teeth may actually penetrate slightly into the surface of the gripped tissue or vessel, without penetrating so deeply as to cause puncturing and hemorrhaging. While three rows of teeth 715, 716, 717 are shown, the invention is not limited to any number of rows or teeth aligned in rows. The number, size and configuration of teeth and gaps on the clamping surfaces may vary without departing from the invention. The interdigitating or interfitting teeth penetrate into the surface of the tissue or vessel to provide enhanced resistance to dislodgement.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. A surgical clip comprising
   a hinge;
   a pair of opposed arms comprising
      a first arm, and
      a second arm, each arm having a clamping side, such that each arm is attached to the hinge, each arm having a free end;
   a head lock comprising
      a tissue spreading male locking pin near the free end one arm, and
      a female aperture near the free end of the opposite arm, such that the female aperture is configured to engage a portion of the male locking pin; and
   a hinge lock comprising
      at least one latching element provided on the first arm or the second arm, and
      at least one catch element provided on the second arm or the first arm, such that the latching element is configured to engage the catch element when the clip is closed; wherein the clamping side of one arm comprises a longitudinally-oriented wedge with a plurality of step features vertically offset on each side of the wedge; and the clamping side of the second arm comprises a longitudinally-oriented V-shaped trough with a plurality of step features vertically offset on each side of the V-shaped trough.

2. The surgical clip of claim 1 wherein the female aperture comprises an elongated slot.

3. The surgical clip of claim 1 wherein the longitudinally-oriented V-shaped trough comprises a bottom window.

4. The surgical clip of claim 1 wherein the female aperture further comprises a plurality of tissue anchor features.

5. A surgical clip comprising
   a hinge;
   a pair of opposed arms comprising
      a first arm, and
      a second arm, each arm having a clamping side, such that each arm is attached to the hinge, each arm having a free end; and
   a head lock comprising
      a male locking pin near the free end one arm, said male locking pin including a tissue spreading head, and
      a female aperture near the free end of the opposite arm, such that the female aperture is configured to engage a portion of the male locking pin, the female aperture comprising a longitudinally-elongated slot, such that the tissue spreading head is configured to penetrate and spread tissue in the path of the male locking pin when the male locking pin is urged towards the female aperture; wherein the clamping side of one arm comprises a longitudinally-oriented wedge with a plurality of step features vertically offset on each side of the wedge; and the clamping side of the second arm comprises a longitudinally-oriented V-shaped trough with a plurality of step features vertically offset on each side of the V-shaped trough.

6. The surgical clip of claim 5, wherein the female aperture further comprises a plurality of tissue anchor features.

7. The surgical clip of claim 5 further comprising
   a hinge lock comprising
      at least one latching element provided on the first arm or the second arm, and at least one catch element provided on the second arm or the first arm, such that the latching element is configured to engage the catch element when the clip is closed.

8. The surgical clip of claim 5 wherein the longitudinally-oriented V-shaped trough comprises a bottom window.

9. A surgical clip comprising
   a hinge;
   a pair of opposed arms comprising
      a first arm having a clamping side comprising a longitudinally-oriented wedge with a plurality of step features vertically offset on each side of the wedge, and
      a second arm having a clamping side comprising a longitudinally-oriented V-shaped trough with a plurality of step features vertically offset on each side of the V-shaped trough, the V-shaped trough conforms to the shape of the wedge, such that each arm is attached to the hinge, each arm having a free end;
   a head lock comprising
      a male locking pin near the free end one arm, said male locking pin including a tissue spreading head aperture, and
      a female aperture near the free end of the opposite arm, such that the female aperture is configured to engage a portion of the male locking pin, such that the tissue spreading head is configured to penetrate and spread tissue in the path of the male locking pin when the male locking pin is urged towards the female aperture; and
   a hinge lock comprising
      at least one latching element provided on the first arm or the second arm, and at least one catch element provided on the second arm or the first arm, such that the latching element is configured to engage the catch element when the clip is closed.

10. The surgical clip of claim 9 wherein the female aperture further comprises a plurality of tissue anchor features.

11. The surgical clip of claim 9 wherein the longitudinally-oriented V-shaped trough comprises a bottom window.

* * * * *